US012643896B2

(12) United States Patent
Frost et al.

(10) Patent No.: US 12,643,896 B2
(45) Date of Patent: Jun. 2, 2026

(54) DICYCLOPROPYLMETHYL DERIVATIVES AS IL-17 MODULATORS

(71) Applicant: UCB Biopharma SRL, Brussels (BE)

(72) Inventors: James Richard Frost, Slough (GB); Gregory William Haslett, Slough (GB); James Thomas Reuberson, Slough (GB)

(73) Assignee: UCB Biopharma SRL, Brussels (BE)

( * ) Notice: Subject to any disclaimer, the term of this patent is extended or adjusted under 35 U.S.C. 154(b) by 482 days.

(21) Appl. No.: 18/035,332

(22) PCT Filed: Nov. 1, 2021

(86) PCT No.: PCT/EP2021/080251

§ 371 (c)(1),
(2) Date: May 4, 2023

(87) PCT Pub. No.: WO2022/096412

PCT Pub. Date: May 12, 2022

(65) Prior Publication Data

US 2023/0399328 A1 Dec. 14, 2023

(30) Foreign Application Priority Data

Nov. 9, 2020 (GB) .................................... 2017642
Jun. 22, 2021 (GB) .................................... 2108945

(51) Int. Cl.
*C07D 471/04* (2006.01)

(52) U.S. Cl.
CPC .................................. *C07D 471/04* (2013.01)

(58) Field of Classification Search
CPC .................................................. C07D 471/04
USPC .................................................. 514/303
See application file for complete search history.

(56) References Cited

FOREIGN PATENT DOCUMENTS

| | | | |
|---|---|---|---|
| WO | WO 2019138017 | 7/2019 | |
| WO | WO-2019138017 A1 * | 7/2019 | ........... C07D 403/14 |
| WO | 2020/127685 | 6/2020 | |

OTHER PUBLICATIONS

International Search Report for PCT/EP2021080251 dated Jan. 11, 2022, 2 pages.

English translation of Office Action of Japanese Patent Application No. JP 2023-527430 dated Aug. 14, 2025, pp. 1-2.

* cited by examiner

*Primary Examiner* — Niloofar Rahmani
(74) *Attorney, Agent, or Firm* — McDonnell Boehnen Hulbert & Berghoff LLP

(57) ABSTRACT

A series of substituted dicyclopropyl methyl derivatives as defined herein, being potent modulators of human IL-17 activity, are accordingly of benefit in the treatment and/or prevention of various human ailments, including inflammatory and autoimmune disorders.

(I)

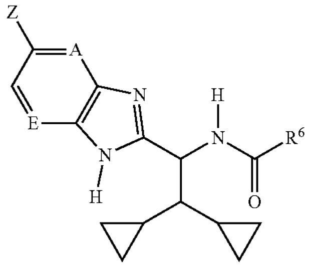

7 Claims, No Drawings

DICYCLOPROPYLMETHYL DERIVATIVES AS IL-17 MODULATORS

CROSS-REFERENCE TO RELATED APPLICATIONS

This application is a U.S. national phase of International Application No. PCT/EP2021/080251, filed Nov. 1, 2021, which claims priority from Great Britain patent application no. GB 2017642.6, filed Nov. 9, 2020, and Great Britain patent application no. GB 2108945.3, filed Jun. 22, 2021, the disclosure of each of which is hereby incorporated by reference in its entirety.

The present invention relates to heterocyclic compounds, and to their use in therapy. More particularly, this invention is concerned with pharmacologically active substituted dicyclopropylmethyl derivatives. These compounds act as modulators of IL-17 activity, and are accordingly of benefit as pharmaceutical agents for the treatment and/or prevention of pathological conditions, including adverse inflammatory and autoimmune disorders.

IL-17A (originally named CTLA-8 and also known as IL-17) is a pro-inflammatory cytokine and the founder member of the IL-17 family (Rouvier et al., *J. Immunol.,* 1993, 150, 5445-5456). Subsequently, five additional members of the family (IL-17B to IL-17F) have been identified, including the most closely related, IL-17F (ML-1), which shares approximately 55% amino acid sequence homology with IL-17A (Moseley et al., *Cytokine Growth Factor Rev.,* 2003, 14, 155-174). IL-17A and IL-17F are expressed by the recently defined autoimmune related subset of T helper cells, Th17, that also express IL-21 and IL-22 signature cytokines (Korn et al., *Ann. Rev. Immunol.,* 2009, 27, 485-517). IL-17A and IL-17F are expressed as homodimers, but may also be expressed as the IL-17A/F heterodimer (Wright et al., *J. Immunol.,* 2008, 181, 2799-2805). IL-17A and F signal through the receptors IL-17R, IL-17RC or an IL-17RA/RC receptor complex (Gaffen, *Cytokine,* 2008, 43, 402-407). Both IL-17A and IL-17F have been associated with a number of autoimmune diseases.

The compounds in accordance with the present invention, being potent modulators of human IL-17 activity, are therefore beneficial in the treatment and/or prevention of various human ailments, including inflammatory and autoimmune disorders.

Furthermore, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/116682 and WO 2014/066726 relate to separate classes of chemical compounds that are stated to modulate the activity of IL-17 and to be useful in the treatment of medical conditions, including inflammatory diseases.

WO 2018/229079 and WO 2020/011731 describe spirocyclic molecules that are stated to act as modulators of IL-17 activity, and thus to be of benefit in the treatment of pathological conditions including adverse inflammatory and autoimmune disorders.

WO 2019/138017 describes a class of fused bicyclic imidazole derivatives, including benzimidazole derivatives and analogues thereof, that are stated to act as modulators of IL-17 activity, and thus to be of benefit in the treatment of pathological conditions including adverse inflammatory and autoimmune disorders.

WO 2019/223718 describes heterocyclic compounds, including benzimidazole derivatives, that are stated to inhibit IL-17A and to be useful as immunomodulators.

Heterocyclic compounds stated to be capable of modulating IL-17 activity are also described in WO 2020/127685, WO 2020/146194 and WO 2020/182666.

WO 2020/120140 and WO 2020/120141, and co-pending international patent applications PCT/IB2020/055970, PCT/EP2020/067758 and PCT/EP2020/067759 (all published on 30 Dec. 2020, as WO 2020/261141, WO 2020/260425 and WO 2020/260426 respectively), describe discrete classes of chemical compounds that are stated to act as modulators of IL-17 activity, and thus to be of benefit in the treatment of pathological conditions including adverse inflammatory and autoimmune disorders.

None of the prior art available to date, however, discloses or suggests the precise structural class of substituted dicyclopropylmethyl derivatives as provided by the present invention.

As well as being potent modulators of human IL-17 activity, the compounds in accordance with the present invention also possess other notable advantages. In particular, the compounds of the invention display valuable metabolic stability, as determined in either microsomal or hepatocyte incubations.

The present invention provides a compound of formula (I) or an N-oxide thereof, or a pharmaceutically acceptable salt thereof:

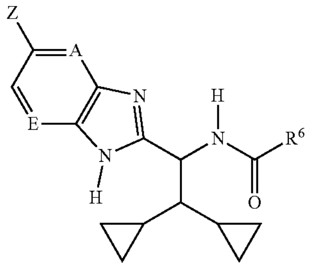

(I)

wherein

A represents C—$R^1$ or N;

E represents C—$R^2$ or N;

Z represents a group of formula (Za), (Zb), (Zc), (Zd), (Ze) or (Zf):

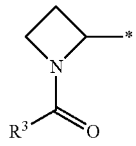

(Za)

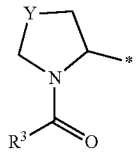

(Zb)

-continued (Zc)

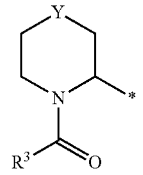

(Zd)

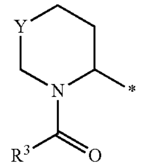

(Ze)

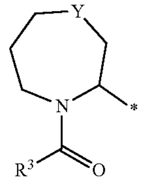

(Zf)

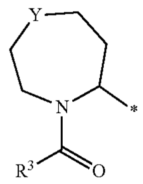

in which the asterisk (*) represents the point of attachment to the remainder of the molecule;

Y represents O, N—$R^4$, $CR^{5a}R^{5b}$, S, S(O), $S(O)_2$ or S(O)(N—$R^7$);

$R^1$ represents hydrogen or fluoro;

$R^2$ represents hydrogen or fluoro;

$R^3$ represents $C_{3-9}$ cycloalkyl, $C_{4-12}$ bicycloalkyl, $C_{3-7}$ heterocycloalkyl or $C_{4-9}$ heterobicycloalkyl, any of which groups may be optionally substituted by one or more substituents;

$R^4$ represents —$COR^4$a, —$CO_2R^{4a}$ or —$SO_2R^{4b}$; or $R^4$ represents hydrogen; or $R^4$ represents $C_{1-6}$ alkyl or $C_{3-9}$ cycloalkyl, either of which groups may be optionally substituted by one or more fluorine atoms;

$R^{4a}$ represents $C_{1-6}$ alkyl, optionally substituted by one or more fluorine atoms;

$R^{4b}$ represents $C_{1-6}$ alkyl;

$R^{5a}$ represents hydrogen, fluoro, methyl, difluoromethyl or trifluoromethyl; and $R^{5b}$ represents hydrogen, fluoro, methyl or hydroxy; or $R^{5a}$ and $R^{5b}$, when taken together with the carbon atom to which they are both attached, represent cyclopropyl;

$R^6$ represents —$OR^{6a}$ or —$NR^{6b}R^{6c}$; or $R^6$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents;

$R^{6a}$ represents $C_{1-6}$ alkyl; or $R^{6a}$ represents $C_{3-9}$ cycloalkyl, which group may be optionally substituted by one or more substituents;

$R^{6b}$ represents hydrogen or $C_{1-6}$ alkyl;

$R^{6c}$ represents hydrogen or $C_{1-6}$ alkyl; and $R^7$ represents $C_{1-6}$ alkyl.

The present invention also provides a compound of formula (I) as defined above, or a pharmaceutically acceptable salt thereof.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of IL-17 function is indicated.

The present invention also provides the use of a compound of formula (I) as defined above or an N-oxide thereof, or a pharmaceutically acceptable salt thereof, for the manufacture of a medicament for the treatment and/or prevention of disorders for which the administration of a modulator of IL-17 function is indicated.

The present invention also provides a method for the treatment and/or prevention of disorders for which the administration of a modulator of IL-17 function is indicated which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Generally, such groups will be unsubstituted, or substituted by one, two, three or four substituents. Typically, such groups will be unsubstituted, or substituted by one, two or three substituents. Suitably, such groups will be unsubstituted, or substituted by one or two substituents.

For use in medicine, the salts of the compounds of formula (I) will be pharmaceutically acceptable salts. Other salts may, however, be useful in the preparation of the compounds of formula (I) or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of formula (I) include acid addition salts which may, for example, be formed by mixing a solution of a compound of formula (I) with a solution of a pharmaceutically acceptable acid.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The term "$C_{3-9}$ cycloalkyl" as used herein refers to monovalent groups of 3 to 9 carbon atoms derived from a saturated monocyclic hydrocarbon, and may comprise benzo-fused analogues thereof. Suitable $C_{3-9}$ cycloalkyl groups include cyclopropyl, cyclobutyl, benzocyclobutenyl, cyclopentyl, indanyl, cyclohexyl, cycloheptyl, cyclooctyl and cyclononanyl.

The term "$C_{4-12}$ bicycloalkyl" as used herein refers to monovalent groups of 4 to 12 carbon atoms derived from a saturated bicyclic hydrocarbon. Typical bicycloalkyl groups include bicyclo[1.1.1]pentanyl, bicyclo[3.1.0]hexanyl, bicyclo[4.1.0]heptanyl and bicyclo[2.2.2]octanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]-pyrazinyl, homopiperazinyl, morpholinyl, benzoxazinyl, thiomorpholinyl, azepanyl, oxazepanyl, diazepanyl, thiadiazepanyl and azocanyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 6-oxabicyclo[3.1.0]hexanyl, 3-azabicyclo[3.1.0]hexanyl, 2-oxa-5-azabicyclo[2.2.1]-heptanyl, 6-azabicyclo[3.2.0]heptanyl, 6-oxabicyclo[3.1.1]heptanyl, 3-azabicyclo[3.1.1]-heptanyl, 3-azabicyclo[4.1.0]heptanyl, 2-oxabicyclo[2.2.2]octanyl, quinuclidinyl, 2-oxa-5-azabicyclo[2.2.2]octanyl, 8-oxabicyclo[3.2.1]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]-octanyl, 3,6-diazabicyclo[3.2.2]nonanyl, 3-oxa-7-azabicyclo[3.3.1]nonanyl, 3,7-dioxa-9-azabicyclo[3.3.1]nonanyl and 3,9-diazabicyclo[4.2.1]nonanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b]-[1,4]dioxinyl, dibenzothienyl, pyrrolyl, indolyl, pyrrolo[2,3-b]pyridinyl, pyrrolo[3,2-c]-pyridinyl, pyrrolo[3,4-b]pyridinyl, pyrazolyl, pyrazolo[1,5-a]pyridinyl, pyrazolo[3,4-d]-pyrimidinyl, pyrazolo[1,5-a]pyrazinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]-pyridinyl, imidazo[1,2-b]pyridazinyl, purinyl, imidazo[1,2-a]pyrimidinyl, imidazo[1,2-c]-pyrimidinyl, imidazo[1,2-a]pyrazinyl, oxadiazolyl, thiadiazolyl, triazolyl, [1,2,4]triazolo-[1,5-a]pyrimidinyl, 6,8-dihydro-5H-[1,2,4]triazolo[4,3-a]pyrazinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C{=}O$)↔enol ($CH{=}CHOH$) tautomers or amide ($NHC{=}O$)↔hydroxyimine ($N{=}COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^{1}H$, $^{2}H$ (deuterium) or $^{3}H$ (tritium) atom, preferably $^{1}H$. Similarly, by way of example, each individual carbon atom present in formula (I), or in the formulae depicted hereinafter, may be present as a $^{12}C$, $^{13}C$ or $^{14}C$ atom, preferably $^{12}C$.

In one embodiment, A represents C—$R^1$. In another embodiment, A represents N.

In one embodiment, E represents C—$R^2$. In another embodiment, E represents N.

In a particular embodiment, A represents C—$R^1$ or N; and E represents C—$R^2$. In one aspect of that embodiment, A represents N; and E represents C—$R^2$.

Suitably, the present invention provides a compound of formula (I-1) or (I-2) or an N-oxide thereof, or a pharmaceutically acceptable salt thereof:

(I-1)

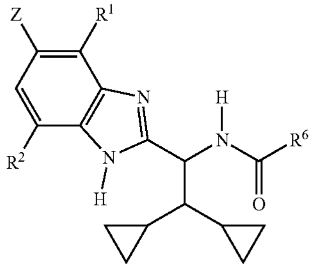

-continued (I-2)

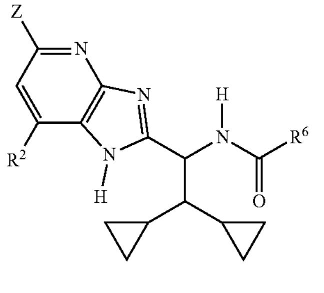

wherein Z, $R^1$, $R^2$ and $R^6$ are as defined above.

In a first embodiment, Z represents a group of formula (Za). In a second embodiment, Z represents a group of formula (Zb). In a third embodiment, Z represents a group of formula (Zc). In a fourth embodiment, Z represents a group of formula (Zd). In a fifth embodiment, Z represents a group of formula (Ze). In a sixth embodiment, Z represents a group of formula (Zf).

Suitably, Z represents a group of formula (Zc).

In a first embodiment, Y represents O. In a second embodiment, Y represents N—$R^4$. In a third embodiment, Y represents $CR^{5a}R^{5b}$. In a fourth embodiment, Y represents S. In a fifth embodiment, Y represents S(O). In a sixth embodiment, Y represents $S(O)_2$. In a seventh embodiment, Y represents S(O)(N—$R^7$).

Typically, Y represents O, N—$R^4$, $CR^{5a}R^{5b}$ or $S(O)_2$, wherein $R^4$, $R^{5a}$ and $R^{5b}$ are as defined above.

Suitably, Y represents $CR^{5a}R^{5b}$, wherein $R^{5a}$ and $R^{5b}$ are as defined above.

In a first embodiment, $R^1$ represents hydrogen. In a second embodiment, $R^1$ represents fluoro.

In a favoured embodiment, $R^2$ represents hydrogen. In another embodiment, $R^2$ represents fluoro.

Typically, $R^3$ represents $C_{3-9}$ cycloalkyl, $C_{4-12}$ bicycloalkyl or $C_{3-7}$ heterocycloalkyl, any of which groups may be optionally substituted by one or more substituents.

Suitably, $R^3$ represents $C_{4-12}$ bicycloalkyl, which group may be optionally substituted by one or more substituents.

Typical examples of $R^3$ include cyclobutyl, bicyclo[1.1.1]pentanyl, azetidinyl, pyrrolidinyl, tetrahydropyranyl and morpholinyl, any of which groups may be optionally substituted by one or more substituents.

Suitable examples of $R^3$ include bicyclo[1.1.1]pentanyl, which group may be optionally substituted by one or more substituents.

Typical examples of optional substituents on $R^3$ include one, two, three or four substituents independently selected from halogen.

Typical examples of particular substituents on $R^3$ include one, two, three or four substituents independently selected from fluoro.

Typical values of $R^3$ include difluorocyclobutyl, fluorobicyclo[1.1.1]pentanyl, difluoroazetidinyl, difluoropyrrolidinyl, tetrafluoropyrrolidinyl, difluorotetrahydropyranyl and tetrafluoromorpholinyl.

Suitable values of $R^3$ include fluorobicyclo[1.1.1]pentanyl.

Generally, $R^4$ represents —$COR^{4a}$, —$CO_2R^{4a}$ or —$SO_2R^{4b}$; or $R^4$ represents hydrogen; or $R^4$ represents $C_{1-6}$ alkyl, which group may be optionally substituted by one or more fluorine atoms, generally by one, two or three fluorine atoms, typically by two fluorine atoms.

Suitably, $R^4$ represents —$CO_2R^{4a}$.

In a first embodiment, $R^4$ represents —$COR^{4a}$. In a second embodiment, $R^4$ represents —$CO_2R^{4a}$. In a third embodiment, $R^4$ represents —$CO_2R^{4a}$. In a fourth embodiment, $R^4$ represents hydrogen. In a fifth embodiment, $R^4$ represents $C_{1-6}$ alkyl, optionally substituted by one or more fluorine atoms, typically by one, two or three fluorine atoms. In one aspect of that embodiment, $R^4$ represents unsubstituted $C_{1-6}$ alkyl, especially methyl or ethyl. In another aspect of that embodiment, $R^4$ represents $C_{1-6}$ alkyl substituted by one, two or three fluorine atoms, typically by two fluorine atoms. Examples of that aspect include difluoroethyl. In a sixth embodiment, $R^4$ represents $C_{3-9}$ cycloalkyl, optionally substituted by one or more fluorine atoms, typically by one, two or three fluorine atoms. In one aspect of that embodiment, $R^4$ represents unsubstituted $C_{3-9}$ cycloalkyl, especially cyclopropyl, cyclobutyl, cyclopentyl or cyclohexyl. In another aspect of that embodiment, $R^4$ represents $C_{3-9}$ cycloalkyl substituted by one, two or three fluorine atoms, typically by two fluorine atoms. Examples of that aspect include difluorocyclobutyl.

Typically, $R^{4a}$ represents $C_{1-6}$ alkyl, optionally substituted by one, two or three fluorine atoms.

Suitably, $R^{4a}$ represents $C_{1-6}$ alkyl or difluoro($C_{1-6}$)alkyl.

In a first embodiment, $R^{4a}$ represents $C_{1-6}$ alkyl, especially methyl or ethyl. In a first aspect of that embodiment, $R^{4a}$ represents methyl. In a second aspect of that embodiment, $R^{4a}$ represents ethyl. In a second embodiment, $R^{4a}$ represents difluoro($C_{1-6}$)-alkyl, especially difluoroethyl.

Particular values of $R^{4a}$ include methyl and difluoroethyl.

Suitably, $R^{4b}$ represents methyl or ethyl. In a first embodiment, $R^{4b}$ represents methyl. In a second embodiment, $R^{4b}$ represents ethyl.

In a first embodiment, $R^{5a}$ represents hydrogen. In a second embodiment, $R^{5a}$ represents fluoro. In a third embodiment, $R^{5a}$ represents methyl. In a fourth embodiment, $R^{5a}$ represents difluoromethyl. In a fifth embodiment, $R^{5a}$ represents trifluoromethyl.

Generally, $R^{5a}$ represents hydrogen, fluoro, difluoromethyl or trifluoromethyl.

Typically, $R^{5a}$ represents hydrogen, fluoro or trifluoromethyl.

Appositely, $R^{5a}$ represents fluoro, difluoromethyl or trifluoromethyl.

Suitably, $R^{5a}$ represents fluoro or trifluoromethyl.

In a first embodiment, $R^{5b}$ represents hydrogen. In a second embodiment, $R^{5b}$ represents fluoro. In a third embodiment, $R^{5b}$ represents methyl. In a fourth embodiment, $R^{5b}$ represents hydroxy.

Typically, $R^{5b}$ represents hydrogen, fluoro or hydroxy.

Suitably, $R^{5b}$ represents fluoro or hydroxy.

Alternatively, $R^{5a}$ and $R^{5b}$ may together form a spiro linkage. Thus, $R^{5a}$ and $R^{5b}$, when taken together with the carbon atom to which they are both attached, may represent cyclopropyl.

Typically, $R^6$ represents —$OR^{6a}$ or —$NR^{6b}R^{6c}$; or $R^6$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, heteroaryl or heteroaryl-($C_{1-6}$)alkyl, any of which groups may be optionally substituted by one or more substituents.

Appositely, $R^6$ represents —$OR^{6a}$; or $R^6$ represents $C_{3-9}$ cycloalkyl, aryl or heteroaryl, any of which groups may be optionally substituted by one or more substituents.

More aptly, $R^6$ represents —$OR^{6a}$; or $R^6$ represents $C_{3-9}$ cycloalkyl or heteroaryl, either of which groups may be optionally substituted by one or more substituents.

Suitably, $R^6$ represents —$OR^{6a}$; or $R^6$ represents heteroaryl, which group may be optionally substituted by one or more substituents.

In a first embodiment, $R^6$ represents optionally substituted $C_{1-6}$ alkyl. In a second embodiment, $R^6$ represents optionally substituted $C_{3-9}$ cycloalkyl. In a third embodiment, $R^6$ represents optionally substituted $C_{3-9}$ cycloalkyl($C_{1-6}$)alkyl. In a fourth embodiment, $R^6$ represents optionally substituted aryl. In a fifth embodiment, $R^6$ represents optionally substituted aryl($C_{1-6}$)alkyl. In a sixth embodiment, $R^6$ represents optionally substituted $C_{3-7}$ heterocycloalkyl. In a seventh embodiment, $R^6$ represents optionally substituted $C_{3-7}$ heterocycloalkyl($C_{1-6}$)alkyl. In an eighth embodiment, $R^6$ represents optionally substituted heteroaryl. In a ninth embodiment, $R^6$ represents optionally substituted heteroaryl($C_{1-6}$) alkyl. In a tenth embodiment, $R^6$ represents —$OR^{6a}$. In an eleventh embodiment, $R^6$ represents —$NR^{6a}R^{6b}$.

Typical examples of $R^6$ include —$OR^{6a}$ or —$NR^{6a}R^{6b}$; and methyl, ethyl, propyl, 2-methylpropyl, butyl, cyclopropyl, cyclobutyl, cyclohexyl, cyclohexylmethyl, phenyl, benzyl, phenylethyl, pyrazolyl, isoxazolyl, oxadiazolyl, pyridinyl, triazolylmethyl, benzotriazolylmethyl or pyridinylmethyl, any of which groups may be optionally substituted by one or more substituents.

Apposite examples of $R^6$ include —$OR^{6a}$; and cyclopropyl, phenyl, pyrazolyl, isoxazolyl or oxadiazolyl, any of which groups may be optionally substituted by one or more substituents.

Illustrative examples of $R^6$ include cyclopropyl and oxadiazolyl, either of which groups may be optionally substituted by one or more substituents.

Particular values of $R^6$ include oxadiazolyl, which group may be optionally substituted by one or more substituents.

Typical examples of optional substituents on $R^6$ include one, two or three substituents independently selected from halogen, cyano, nitro, $C_{1-6}$ alkyl, trifluoro-methyl, phenyl, fluorophenyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$) alkyl, $C_{1-6}$ alkylamino, di($C_{1-6}$)alkylamino, pyrrolidinyl, tetrahydropyranyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl and di-($C_{1-6}$)alkylsulfoximinyl.

Apposite examples of optional substituents on $R^6$ include one, two or three substituents independently selected from halogen, $C_{1-6}$ alkyl and trifluoromethyl.

Suitable examples of optional substituents on $R^6$ include one, two or three substituents independently selected from $C_{1-6}$ alkyl and trifluoromethyl.

Typical examples of particular substituents on $R^6$ include one, two or three substituents independently selected from fluoro, chloro, bromo, cyano, nitro, methyl, ethyl, isopropyl, tert-butyl, trifluoromethyl, phenyl, fluorophenyl, hydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, tetrahydropyranyl, morpholinyl, piperazinyl, acetylamino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl, dimethylaminosulfonyl and dimethylsulfoximinyl.

Apposite examples of particular substituents on $R^6$ include one, two or three substituents independently selected from fluoro, methyl, ethyl and trifluoromethyl.

Illustrative examples of particular substituents on $R^6$ include one, two or three substituents independently selected from fluoro, methyl and trifluoromethyl.

Suitable examples of particular substituents on $R^6$ include one, two or three substituents independently selected from methyl and trifluoromethyl.

Illustrative examples of particular values of $R^6$ include methyl, difluoromethyl, methylsulfonylmethyl, aminomethyl, methylaminomethyl, difluoroethyl, carboxyethyl, difluoropropyl, 2-methylpropyl, butyl, cyanocyclopropyl, methylcyclopropyl, ethyl-cyclopropyl, dimethylcyclopropyl, trifluoromethylcyclopropyl, phenylcyclopropyl, fluorophenylcyclopropyl, hydroxycyclopropyl, aminocyclopropyl, cyclobutyl, trifluoromethylcyclobutyl, cyclohexyl, cyclohexylmethyl, phenyl, fluorophenyl, chloro-phenyl, cyanophenyl, methylphenyl, hydroxyphenyl, methylsulfonylphenyl, dimethyl-sulfoximinylphenyl, benzyl, fluorobenzyl, difluorobenzyl, chlorobenzyl, (chloro)(fluoro)-benzyl, dichlorobenzyl, (chloro)(difluoro)benzyl, bromobenzyl, cyanobenzyl, methyl-benzyl, dimethylbenzyl, trifluoromethylbenzyl, phenylbenzyl, hydroxybenzyl, hydroxymethylbenzyl, benzoyl, methoxybenzyl, dimethoxybenzyl, trifluoromethoxy-benzyl, methylsulfonylbenzyl, aminomethylbenzyl, aminoethylbenzyl, dimethylaminobenzyl, pyrrolidinylbenzyl, (dimethyl)(pyrrolidinyl)benzyl, morpholinylbenzyl, (dimethyl)(morpholinyl)benzyl, piperazinylbenzyl, acetylaminoethylbenzyl, phenylethyl, chlorophenylethyl, methylpyrazolyl, ethylpyrazolyl, (methyl)(tetrahydropyranyl)-pyrazolyl, methylisoxazolyl, ethylisoxazolyl, methyloxadiazolyl, ethyloxadiazolyl, pyridinyl, triazolylmethyl, benzotriazolylmethyl, pyridinylmethyl, aminopyridinylmethyl and —$OR^{6a}$. Additional examples include fluorocyclopropyl.

Apposite values of $R^6$ include —$OR^{6a}$, trifluoromethylcyclopropyl, fluorophenyl, methylpyrazolyl, ethylpyrazolyl, methylisoxazolyl, ethylisoxazolyl, methyloxadiazolyl and ethyloxadiazolyl. Additional examples include fluorocyclopropyl.

Illustrative values of $R^6$ include fluorocyclopropyl, trifluoromethylcyclopropyl and methyloxadiazolyl.

Suitable values of $R^6$ include trifluoromethylcyclopropyl and methyloxadiazolyl.

In a first embodiment, $R^{6a}$ represents $C_{1-6}$ alkyl. In a second embodiment, $R^{6a}$ represents optionally substituted $C_9$ cycloalkyl.

Typically, $R^{6a}$ represents $C_{1-6}$ alkyl; or $R^{6a}$ represents cyclobutyl, which group may be optionally substituted by one or more substituents.

Typical examples of optional substituents on $R^{6a}$ include one, two or three substituents independently selected from halogen, cyano, nitro, $C_{1-6}$ alkyl, trifluoro-methyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable examples of optional substituents on $R^{6a}$ include one, two or three substituents independently selected from halogen.

Typical examples of specific substituents on $R^{6a}$ include one, two or three substituents independently selected from fluoro, chloro, bromo, cyano, nitro, methyl, ethyl, isopropyl, tert-butyl, trifluoromethylhydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl.

Suitable examples of specific substituents on $R^{6a}$ include one, two or three substituents independently selected from fluoro.

Illustrative examples of specific values of $R^{6a}$ include methyl, ethyl, n-propyl, isopropyl, n-butyl, tert-butyl, cyclobutyl and difluorocyclobutyl.

Suitably, $R^{6a}$ represents isopropyl.

Typically, $R^{6a}$ represents cyclobutyl.

Typically, $R^{6b}$ represents hydrogen or methyl.

In a first embodiment, $R^{6b}$ represents hydrogen. In a second embodiment, $R^{6b}$ represents $C_{1-6}$ alkyl, especially methyl.

Typically, $R^{6c}$ represents hydrogen or methyl.

In a first embodiment, $R^{6c}$ represents hydrogen. In a second embodiment, $R^{6c}$ represents $C_{1-6}$ alkyl, especially methyl.

Suitably, $R^7$ represents methyl or ethyl. In a first embodiment, $R^7$ represents methyl. In a second embodiment, $R^7$ represents ethyl.

One sub-class of compounds according to the invention is represented by the compounds of formula (IIA) and N-oxides thereof, and pharmaceutically acceptable salts thereof:

(IIA)

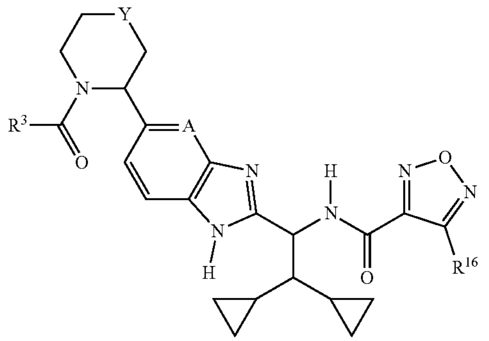

wherein $R^{16}$ represents methyl or ethyl; and

A, Y and $R^3$ are as defined above.

In a first embodiment, $R^{16}$ represents methyl. In a second embodiment, $R^{16}$ represents ethyl.

Another sub-class of compounds according to the invention is represented by the compounds of formula (IIB) and N-oxides thereof, and pharmaceutically acceptable salts thereof:

(IIB)

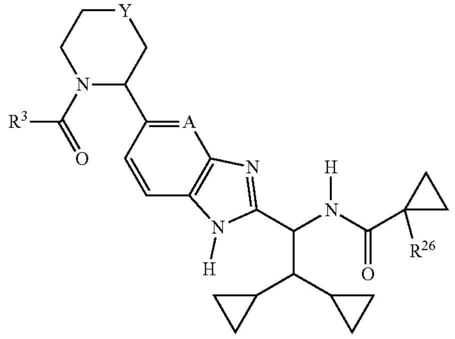

wherein $R^{26}$ represents fluoro or trifluoromethyl; and

A, Y and $R^3$ are as defined above.

In a first embodiment, $R^{26}$ represents fluoro. In a second embodiment, $R^{26}$ represents trifluoromethyl.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments, including inflammatory and autoimmune disorders.

The compounds according to the present invention are useful in the treatment and/or prophylaxis of a pathological disorder that is mediated by a pro-inflammatory IL-17 cytokine or is associated with an increased level of a pro-inflammatory IL-17 cytokine. Generally, the pathological condition is selected from the group consisting of infections (viral, bacterial, fungal and parasitic), endotoxic shock associated with infection, arthritis, rheumatoid arthritis, psoriatic arthritis, systemic onset juvenile idiopathic arthritis (JIA), systemic lupus erythematosus (SLE), asthma, chronic obstructive airways disease (COAD), chronic obstructive pulmonary disease (COPD), acute lung injury, pelvic inflammatory disease, Alzheimer's Disease, Crohn's disease, inflammatory bowel disease, irritable bowel syndrome, ulcerative colitis, Castleman's disease, axial spondyloarthritis, ankylosing spondylitis and other spondyloarthropathies, dermatomyositis, myocarditis, uveitis, exophthalmos, autoimmune thyroiditis, Peyronie's Disease, coeliac disease, gall bladder disease, Pilonidal disease, peritonitis, psoriasis, atopic dermatitis, hidradenitis suppurativa, vasculitis, surgical adhesions, stroke, autoimmune diabetes, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, fibrosing disorders including pulmonary fibrosis, liver fibrosis, renal fibrosis, scleroderma or systemic sclerosis, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, chronic lymphatic leukemia, gastric cancer and colon cancer), heart disease including ischaemic diseases such as myocardial infarction as well as atherosclerosis, intravascular coagulation, bone resorption, osteoporosis, periodontitis, hypochlorhydia and pain (particularly pain associated with inflammation).

WO 2009/089036 reveals that modulators of IL-17 activity may be administered to inhibit or reduce the severity of ocular inflammatory disorders, in particular ocular surface inflammatory disorders including Dry Eye Syndrome (DES). Consequently, the compounds in accordance with the present invention are useful in the treatment and/or prevention of an IL-17-mediated ocular inflammatory disorder, in particular an IL-17-mediated ocular surface inflammatory disorder including Dry Eye Syndrome. Ocular surface inflammatory disorders include Dry Eye Syndrome, penetrating keratoplasty, corneal transplantation, lamellar or partial thickness transplantation, selective endothelial transplantation, corneal neovascularization, keratoprosthesis surgery, corneal ocular surface inflammatory conditions, conjunctival scarring disorders, ocular autoimmune conditions, Pemphigoid syndrome, Stevens-Johnson syndrome, ocular allergy, severe allergic (atopic) eye disease, conjunctivitis and microbial keratitis. Particular categories of Dry Eye Syndrome include keratoconjunctivitis sicca (KCS), Sjögren syndrome, Sjögren syndrome-associated keratoconjunctivitis sicca, non-Sjögren syndrome-associated keratoconjunctivitis sicca, keratitis sicca, sicca syndrome, xerophthalmia, tear film disorder, decreased tear production, aqueous tear deficiency (ATD), meibomian gland dysfunction and evaporative loss.

Illustratively, the compounds of the present invention may be useful in the treatment and/or prophylaxis of a pathological disorder selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, hidradenitis suppurativa, scleroderma, systemic sclerosis, lung fibrosis, inflammatory bowel diseases (including Crohn's disease and ulcerative colitis), axial spondyloarthritis, ankylosing spondylitis and other spondyloarthropathies, cancer and pain (particularly pain associated with inflammation).

Suitably, the compounds of the present invention are useful in the treatment and/or prophylaxis of psoriasis, psoriatic arthritis, hidradenitis suppurativa, axial spondyloarthritis or ankylosing spondylitis.

The present invention also provides a pharmaceutical composition which comprises a compound in accordance with the invention as described above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds according to the present invention may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds according to the present invention may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration the compounds according to the present invention may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound according to the present invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above may be prepared by a process which comprises reacting a carboxylic acid of formula $R^6$—$CO_2H$ with a compound of formula (III):

(III)

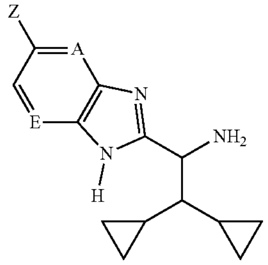

wherein Z, A, E and $R^6$ are as defined above.

The reaction is conveniently accomplished in the presence of a coupling agent and a base. Suitable coupling agents include 1-[bis(dimethylamino)methylene]-1H-1,2,3-triazolo[4,5-b]pyridinium 3-oxid hexafluorophosphate (HATU); and 2,4,6-tripropyl-1,3,5,2,4,6-trioxatriphosphorinane-2,4,6-trioxide. Suitable bases include organic amines, e.g. a trialkylamine such as N,N-diisopropylethylamine; and pyridine. The reaction is conveniently performed at ambient or elevated temperature in a suitable solvent, e.g. a cyclic ether such as tetrahydrofuran; or a dipolar aprotic solvent such as N,N-dimethylformamide or N,N-dimethylacetamide; or a chlorinated solvent such as dichloromethane; or an organic ester solvent such as ethyl acetate.

Alternatively, the compounds of formula (I) above may be prepared by a process which comprises reacting a compound of formula $R^6$—COCl, e.g. acetyl chloride, or 2-fluorobenzoyl chloride, or isopropyl chloroformate, with a compound of formula (III) as defined above. The reaction is conveniently accomplished in the presence of a base.

Suitable bases include organic amines, e.g. a trialkylamine such as N,N-diisopropylethylamine. The reaction is conveniently performed at ambient temperature in a suitable solvent, e.g. a chlorinated solvent such as dichloromethane, or a cyclic ether such as tetrahydrofuran.

Where $R^6$ represents —$OR^{6a}$, the compounds of formula (I) above may be prepared by a two-step process which comprises: (i) reacting a compound of formula $R^{6a}$—OH with N,N'-disuccinimidyl carbonate, ideally in the presence of a base, e.g. an organic amine such as triethylamine; and (ii) reacting the resulting material with a compound of formula (III) as defined above. Steps (i) and (ii) are conveniently performed at ambient temperature in a suitable solvent, e.g. a chlorinated solvent such as dichloromethane, or an organic nitrile solvent such as acetonitrile.

In an alternative procedure, the compounds of formula (I) above may be prepared by a process which comprises reacting a carboxylic acid of formula $R^3$—$CO_2H$ with a compound of formula (IV):

(IV)

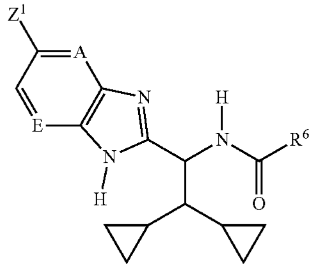

wherein $Z^1$ represents a group of formula (Za-1), (Zb-1), (Zc-1), (Zd-1), (Ze-1) or (Zf-1):

(Za-1)

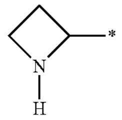

(Zb-1)

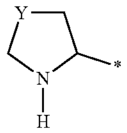

(Zc-1)

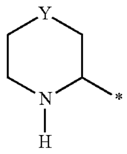

(Zd-1)

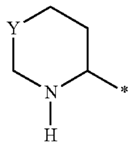

(Ze-1)

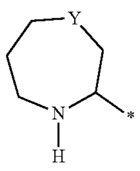

(Zf-1)

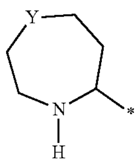

in which the asterisk (*) represents the point of attachment to the remainder of the molecule; and A, E, Y, $R^3$ and $R^6$ are as defined above;

under conditions analogous to those described above for the reaction between compound (III) and a carboxylic acid of formula $R^6$—$CO_2H$.

In an alternative procedure, the compounds of formula (I) above may be prepared by a process which comprises cyclising a compound of formula (VA) or (VB):

(VA)+

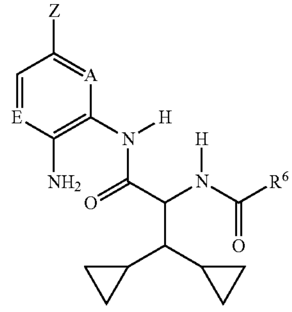

(VB)

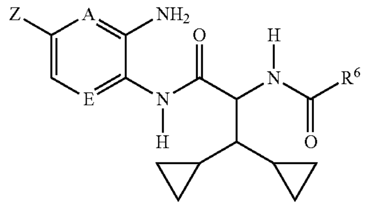

wherein Z, A, E and $R^6$ are as defined above.

Cyclisation of compound (VA) or (VB) is conveniently effected by heating in a suitable medium, e.g. acetic acid, or trifluoroacetic acid.

The intermediates of formula (VA) or (VB) above may be prepared by reacting a compound of formula (VI) with a carboxylic acid of formula (VII) or a salt thereof, e.g. a lithium salt thereof:

(VI)

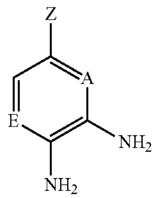

(VII)

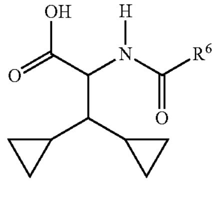

wherein Z, A, E and $R^6$ are as defined above; under conditions analogous to those described above for the reaction between compound (III) and a carboxylic acid of formula $R^6$—$CO_2H$.

The intermediates of formula (VII) may be prepared by a two-step procedure which comprises: (i) reacting a carboxylic acid of formula $R^6$—$CO_2H$ with a compound of formula (VIII):

(VIII)

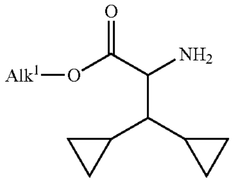

wherein $Alk^1$ represents $C_{1-4}$ alkyl, e.g. methyl or ethyl, and $R^6$ is as defined above; under conditions analogous to those described above for the reaction between compound (III) and a carboxylic acid of formula $R^6$—$CO_2H$; and (ii) saponification of the resulting material by treatment with a base.

Alternative coupling agents that may usefully be employed in step (i) include N-(3-dimethylaminopropyl)-N'-ethylcarbodiimide hydrochloride (EDC·HCl) and O-(benzotriazol-1-yl)-N,N,N',N'-tetramethyluronium hexafluorophosphate (HBTU).

The saponification reaction in step (ii) will generally be effected by treatment with a base. Suitable bases include inorganic hydroxides, e.g. an alkali metal hydroxide such as lithium hydroxide. Where lithium hydroxide is employed in step (ii) of the above procedure, the product may be the lithium salt of the carboxylic acid of formula (VII).

Step (ii) is conveniently effected at ambient temperature in water and a suitable organic solvent, e.g. a cyclic ether such as tetrahydrofuran, optionally in admixture with a $C_{1-4}$ alkanol such as methanol.

The intermediates of formula (III) above may be prepared by a three-step procedure which comprises the following steps:

(i) reacting a compound of formula (VI) as defined above with a compound of formula (IX):

(IX)

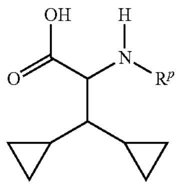

wherein $R^p$ represents a N-protecting group; under conditions analogous to those described above for the reaction between compounds (VI) and (VII);

(ii) cyclisation of the resulting material under conditions analogous to those described above for the cyclisation of compound (VA) or (VB); and (iii) removal of the N-protecting group $R^p$.

The N-protecting group $R^p$ will suitably be tert-butoxycarbonyl (BOC), in which case the removal thereof in step (iii) may conveniently be effected by treatment with an acid, e.g. a mineral acid such as hydrochloric acid, or an organic acid such as trifluoroacetic acid.

Alternatively, the N-protecting group $R^p$ may be benzyloxycarbonyl, in which case the removal thereof may conveniently be effected by catalytic hydrogenation, typically by treatment with hydrogen gas or ammonium formate in the presence of a hydrogenation catalyst, e.g. palladium on charcoal, or palladium hydroxide on charcoal.

The intermediates of formula (IV) above may be prepared by removal of the N-protecting group $R^z$ from a compound of formula (X):

(X)

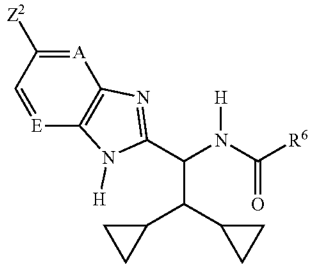

wherein $Z^2$ represents a group of formula (Za-2), (Zb-2), (Zc-2), (Zd-2), (Ze-2) or (Zf-2):

(Za-2)

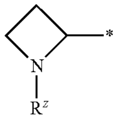

(Zb-2)

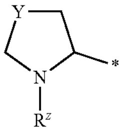

(Zc-2)

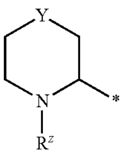

(Zd-2)

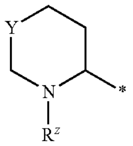

(Ze-2)

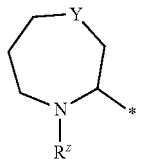

(Zf-2)

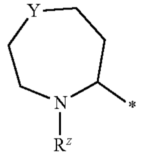

in which the asterisk (*) represents the point of attachment to the remainder of the molecule;

$R^z$ represents a N-protecting group; and

A, E, Y and $R^6$ are as defined above.

The N-protecting group $R^z$ will suitably be tert-butoxycarbonyl (BOC), in which case the removal thereof may conveniently be effected by treatment with an acid, e.g. a mineral acid such as hydrochloric acid, or an organic acid such as trifluoroacetic acid.

The intermediates of formula (X) above may be prepared by a four-step procedure which comprises the following steps:

(i) reacting a compound of formula (IX) as defined above with a compound of formula (XI):

(XI)

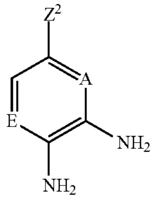

wherein $Z^2$, A and E are as defined above; under conditions analogous to those described above for the reaction between compounds (VI) and (IX);

(ii) cyclisation of the resulting material under conditions analogous to those described above for the cyclisation of compound (VA) or (VB);

(iii) removal of the N-protecting group $R^p$ under conditions analogous to those described above; and (iv) reaction of the material thereby obtained with a carboxylic acid of formula $R^6$—$CO_2H$, under conditions analogous to those described above for the reaction between compound (III) and a carboxylic acid of formula $R^6$—$C_{02}H$.

In the alternative, the intermediates of formula (III) above may be prepared by a procedure which comprises the following steps:

(i) reacting a compound of formula (XII) with the compound of formula (XIII):

(XII)

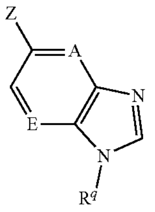

(XIII)

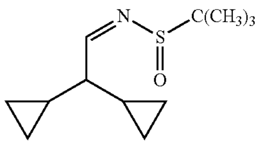

wherein Z, A and E are as defined above, and $R^q$ represents a N-protecting group; to provide a compound of formula (XIV):

(XIV)

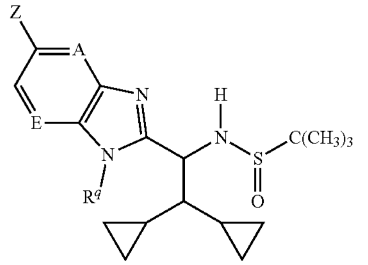

wherein Z, A, E and $R^q$ are as defined above; and (ii) removal of the tert-butylsulfinyl group and the N-protecting group $R^q$ from compound (XIV).

The N-protecting group $R^q$ will suitably be 2-(trimethylsilyl)ethoxymethyl.

Step (i) is suitably effected by treatment of compound (XII) with a base, e.g. an organic base such as n-butyllithium, followed by reaction with compound (XIII). The reaction is conveniently accomplished in a suitable solvent, e.g. a cyclic ether such as tetrahydrofuran.

Where the N-protecting group $R^q$ is 2-(trimethylsilyl)ethoxymethyl, removal of the tert-butylsulfinyl group and the N-protecting group $R^q$ from compound (XIV) in step (ii) may both be accomplished by treatment with an acid, e.g. a mineral acid such as hydrochloric acid.

Where the N-protecting group $R^q$ is 2-(trimethylsilyl)ethoxymethyl, the intermediates of formula (XII) above may be prepared by a procedure which comprises the following steps:

(i) reaction of a compound of formula (VI) as defined above with formic acid; and (ii) reaction of the material thereby obtained with 2-(trimethylsilyl)ethoxymethyl chloride.

Step (i) is conveniently carried out at an elevated temperature.

Step (ii) is suitably effected by treating the reactants with a base, e.g. an inorganic base such as sodium hydride or potassium carbonate.

The intermediate of formula (XIII) above may be prepared by reacting 2,2-dicyclopropylacetaldehyde with 2-methyl-2-propanesulfinamide. The reaction is suitably effected in the presence of pyridinium p-toluenesulfonate and magnesium sulfate. The reaction is conveniently carried out at ambient temperature in a suitable solvent, e.g. a chlorinated solvent such as dichloromethane.

Alternatively, the intermediates of formula (IV) above may be prepared by a procedure which comprises the following steps:

(i) removal of the N-protecting group $R^p$ from a compound of formula (XV):

(XV)

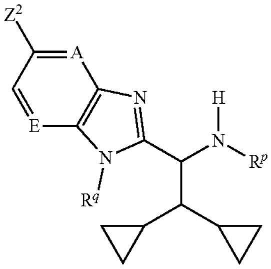

wherein $Z^2$, A, E, $R^p$ and $R^q$ are as defined above; under conditions analogous to those described above;

(ii) reaction of the material thereby obtained with a carboxylic acid of formula $R^6—CO_2H$, under conditions analogous to those described above for the reaction between compound (III) and a carboxylic acid of formula $R^6—CO_2H$; and (iii) removal of the N-protecting groups $R^q$ and $R^z$ from the material thereby obtained.

Where the N-protecting group $R^z$ is BOC, and the N-protecting group $R^q$ is 2-(trimethylsilyl)ethoxymethyl, removal of the N-protecting groups $R^q$ and $R^z$ in step (iii) may both be accomplished by treatment with an acid, e.g. an organic acid such as trifluoroacetic acid.

Alternatively, the intermediates of formula (III) above may be prepared by a procedure which comprises the following steps:

(i) removal of the N-protecting groups $R^q$ and $R^z$ from a compound of formula (XV) as defined above;

(ii) reacting the material thereby obtained with a carboxylic acid of formula $R^3—CO_2H$, under conditions analogous to those described above for the reaction between compound (IV) and a carboxylic acid of formula $R^3—CO_2H$; and (iii) removal of the N-protecting group $R^p$ from the material thereby obtained, under conditions analogous to those described above.

Where the N-protecting group $R^z$ is BOC, and the N-protecting group $R^q$ is 2-(trimethylsilyl)ethoxymethyl, removal of the N-protecting groups $R^q$ and $R^z$ in step (i) may both be accomplished by treatment with an acid, e.g. an organic acid such as trifluoroacetic acid.

The intermediates of formula (XV) above may be prepared by reacting a compound of formula $Z^2—CO_2H$ with a compound of formula (XVI):

(XVI)

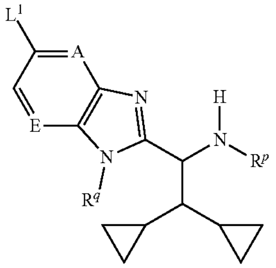

wherein $Z^2$, A, E, $R^p$ and $R^q$ are as defined above, and $L^1$ represents a suitable leaving group; in the presence of a transition metal catalyst.

The leaving group $L^1$ is suitably a halogen atom, e.g. bromo.

Suitable transition metal catalysts of use in the reaction include [4,4'-bis(1,1-dimethylethyl)-2,2'-bipyridine-N1,N1']bis-{3,5-difluoro-2-[5-(trifluoromethyl)-2-pyridinyl-N]phenyl-C}iridium(III) hexafluorophosphate. The reaction will generally be performed in the presence of nickel(II) chloride ethylene glycol dimethyl ether complex and 4,4'-di-tert-butyl-2,2'-dipyridyl. The reaction will suitably be effected in the presence of a base, e.g. an organic base such as 1,8-diazabicyclo[5.4.0]undec-7-ene; and the reactants will typically be exposed to a bright light source. A suitable bright light source will typically comprise the 'integrated photoreactor' described in *ACS Cent. Sci.*, 2017, 3, 647-653. The reaction will conveniently be carried out at ambient temperature in a suitable solvent, e.g. a dipolar aprotic solvent such as N,N-dimethylformamide.

Where the N-protecting group $R^q$ is 2-(trimethylsilyl)ethoxymethyl, the intermediates of formula (XVI) above may be prepared by a procedure which comprises the following steps:

(i) reacting a compound of formula (IX) as defined above with a compound of formula (XVII):

(XVII)

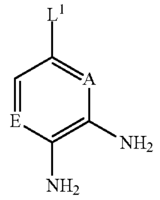

wherein A, E and $L^1$ are as defined above; under conditions analogous to those described above for the reaction between compounds (VI) and (IX);

(ii) cyclisation of the resulting material under conditions analogous to those described above for the cyclisation of compound (VA) or (VB); and (iii) reaction of the material thereby obtained with 2-(trimethylsilyl)ethoxymethyl chloride.

Step (iii) is suitably effected by treating the reactants with a base, e.g. an inorganic base such as sodium hydride or potassium carbonate.

In an alternative approach, the intermediates of formula (III) above may be prepared by a procedure which comprises the following steps:

(i) reacting a compound of formula (IX) as defined above with a compound of formula (XI) as defined above; under conditions analogous to those described above for the reaction between compounds (VI) and (IX);

(ii) cyclisation of the resulting material under conditions analogous to those described above for the cyclisation of compound (VA) or (VB);

(iii) removal of the N-protecting group $R^z$ from the material thereby obtained, under conditions analogous to those described above;

(iv) reacting the material thereby obtained with a carboxylic acid of formula $R^3$—$CO_2H$, under conditions analogous to those described above for the reaction between compound (IV) and a carboxylic acid of formula $R^3$—$CO_2H$; and (v) removal of the N-protecting group $R^p$ from the material thereby obtained, under conditions analogous to those described above.

Where they are not commercially available, the starting materials of formula (VI), (VIII), (IX), (XI) and (XVII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound comprising a N—BOC moiety (wherein BOC is an abbreviation for tert-butoxycarbonyl) may be converted into the corresponding compound comprising a N—H moiety by treatment with an acid, e.g. a mineral acid such as hydrochloric acid, or an organic acid such as trifluoroacetic acid.

A compound comprising a N—H functionality may be alkylated, e.g. methylated, by treatment with a suitable alkyl halide, e.g. iodomethane, typically in the presence of a base, e.g. an inorganic carbonate such as sodium carbonate.

A compound comprising a N—H functionality may be acylated, e.g. acetylated, by treatment with a suitable acyl halide, e.g. acetyl chloride, typically in the presence of a base, e.g. an organic base such as N,N-diisopropylethylamine or triethylamine. Similarly, a compound comprising a N—H functionality may be acylated, e.g. acetylated, by treatment with a suitable acyl anhydride, e.g. acetic anhydride, typically in the presence of a base, e.g. an organic base such as triethylamine.

Similarly, a compound comprising a N—H functionality may be converted into the corresponding compound comprising a N—$S(O)_2Alk^1$ functionality (wherein $Alk^1$ is as defined above) by treatment with the appropriate $C_{1-4}$ alkylsulfonyl chloride reagent, e.g. methylsulfonyl chloride, typically in the presence of a base, e.g. an organic base such as triethylamine.

Similarly, a compound comprising a N—H functionality may be converted into the corresponding compound comprising a carbamate or urea moiety respectively by treatment with the appropriate chloroformate or carbamoyl chloride reagent, typically in the presence of a base, e.g. an organic base such as triethylamine. Alternatively, a compound comprising a N—H functionality may be converted into the corresponding compound comprising a urea moiety by treatment with the appropriate amine-substituted (3-methylimidazol-3-ium-1-yl)methanone iodide derivative, typically in the presence of a base, e.g. an organic base such as triethylamine. Alternatively, a compound comprising a N—H functionality may be converted into the corresponding compound comprising a urea moiety N—C(O)N(H)$Alk^1$ (wherein $Alk^1$ is as defined above) by treatment with the appropriate isocyanate derivative $Alk^1$-N═C═O, typically in the presence of a base, e.g. an organic base such as triethylamine.

A compound comprising a N—H functionality may be converted into the corresponding compound comprising a N—C(H) functionality by treatment with the appropriate aldehyde or ketone in the presence of a reducing agent such as sodium triacetoxyborohydride.

A compound comprising a $C_{1-4}$ alkoxycarbonyl moiety —$CO_2Alk^1$ (wherein $Alk^1$ is as defined above) may be converted into the corresponding compound comprising a carboxylic acid (—$CO_2H$) moiety by treatment with a base, e.g. an alkali metal hydroxide salt such as lithium hydroxide. Alternatively, a compound comprising a tert-butoxycarbonyl moiety may be converted into the corresponding compound comprising a carboxylic acid (—$CO_2H$) moiety by treatment with trifluoroacetic acid.

A compound comprising a carboxylic acid (—$CO_2H$) moiety may be converted into the corresponding compound comprising an amide moiety by treatment with the appropriate amine, under conditions analogous to those described above for the reaction between compound (III) and a carboxylic acid of formula $R^6$—$CO_2H$.

A compound comprising a $C_{1-4}$ alkoxycarbonyl moiety —$CO_2Alk^1$ (wherein $Alk^1$ is as defined above) may be converted into the corresponding compound comprising a hydroxymethyl (—$CH_2OH$) moiety by treatment with a reducing agent such as lithium aluminium hydride.

A compound comprising a $C_{1-4}$ alkylcarbonyloxy moiety —OC(O)$Alk^1$ (wherein $Alk^1$ is as defined above), e.g. acetoxy, may be converted into the corresponding compound comprising a hydroxy (—OH) moiety by treatment with a base, e.g. an alkali metal hydroxide salt such as sodium hydroxide.

A compound comprising a halogen atom, e.g. bromo, may be converted into the corresponding compound comprising an optionally substituted aryl, heterocycloalkenyl or heteroaryl moiety by treatment with the appropriately substituted aryl, heterocycloalkenyl or heteroaryl boronic acid or a cyclic ester thereof formed with an organic diol, e.g. pinacol, 1,3-propanediol or neopentyl glycol. The reaction is typically effected in the presence of a transition metal catalyst, and a base. The transition metal catalyst may be [1,1'-bis(diphenylphosphino)ferrocene]dichloropalladium (II). In the alternative, the transition metal catalyst may be tris(dibenzylideneacetone)dipalladium(0), which may advantageously be employed in conjunction with 2-dicyclohexylphosphino-2',4',6'-triisopropylbiphenyl (XPhos). Suitably, the base may be an inorganic base such as sodium carbonate or potassium carbonate.

A compound comprising a halogen atom, e.g. bromo, may be converted into the corresponding compound comprising an optionally substituted aryl or heteroaryl moiety via a two-step procedure which comprises: (i) reaction with bis (pinacolato)diboron; and (ii) reaction of the compound thereby obtained with an appropriately substituted bromoaryl or bromoheteroaryl derivative. Step (i) is conveniently effected in the presence of a transition metal catalyst such as [1,1'-bis(diphenylphosphino)ferrocene]-dichloropalladium(II), and potassium acetate. Step (ii) is conveniently effected in the presence of a transition metal catalyst such as [1,1'-bis(diphenylphosphino)ferrocene]-dichloropalladium (II), and a base, e.g. an inorganic base such as sodium carbonate or potassium carbonate.

A compound comprising a cyano (—CN) moiety may be converted into the corresponding compound comprising a 1-aminoethyl moiety by a two-step process which comprises: (i) reaction with methylmagnesium chloride, ideally in the presence of titanium(IV) isopropoxide; and (ii) treatment of the resulting material with a reducing agent such as sodium borohydride. If an excess of methylmagnesium chloride is employed in step (i), the corresponding compound comprising a 1-amino-1-methylethyl moiety may be obtained.

A compound comprising the moiety —S— may be converted into the corresponding compound comprising the moiety —S(O)(NH)— by treatment with (diacetoxyiodo) benzene and ammonium carbamate.

A compound comprising a C═C double bond may be converted into the corresponding compound comprising a CH—CH single bond by treatment with gaseous hydrogen in the presence of a hydrogenation catalyst, e.g. palladium on charcoal.

A compound comprising an aromatic nitrogen atom may be converted into the corresponding compound comprising an N-oxide moiety by treatment with a suitable oxidising agent, e.g. 3-chloroperbenzoic acid.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Greene's Protective Groups in Organic Synthesis*, ed. P. G. M. Wuts, John Wiley & Sons, $5^{th}$ edition, 2014. The protecting groups may be removed at any convenient subsequent stage utilising methods known from the art.

The compounds in accordance with this invention potently inhibit IL-17 induced IL-6 release from human dermal fibroblasts. Thus, when tested in the HDF cell line assay described below, compounds of the present invention exhibit a $pIC_{50}$ value of 4.8 or more, generally of 6.0 or more, usually of 7.0 or more, typically of 7.2 or more, suitably of 7.5 or more, ideally of 7.8 or more, and preferably of 8.0 or more ($pIC_{50}$ equals $-\log_{10}[IC_{50}]$, in which $IC_{50}$ is expressed as a molar concentration, so the skilled person will appreciate that a higher $pIC_{50}$ figure denotes a more active compound).

Inhibition of IL-17A Induced IL-6 Release from Dermal Fibroblast Cell Line

The purpose of this assay is to test the neutralising ability to IL-17 proteins, in a human primary cell system. Stimulation of normal human dermal fibroblasts (HDF) with IL-17 alone produces only a very weak signal but in combination with certain other cytokines, such as TNFα, a synergistic effect can be seen in the production of inflammatory cytokines, i.e. IL-6.

HDFs were stimulated with IL-17A (50 pM) in combination with TNF-α (25 pM). The resultant IL-6 response was then measured using a homogenous time-resolved FRET kit from Cisbio. The kit utilises two monoclonal antibodies, one labelled with Eu-Cryptate (Donor) and the second with d2 or XL665 (Acceptor). The intensity of the signal is proportional to the concentration of IL-6 present in the sample (Ratio is calculated by 665/620×104).

The ability of a compound to inhibit IL-17 induced IL-6 release from human dermal fibroblasts is measured in this assay.

HDF cells (Sigma #106-05n) were cultured in complete media (DMEM+10% FCS+2 mM L-glutamine) and maintained in a tissue culture flask using standard techniques. Cells were harvested from the tissue culture flask on the morning of the assay using TrypLE (Invitrogen #12605036). The TrypLE was neutralised using complete medium (45 mL) and the cells were centrifuged at 300×g for 3 minutes. The cells were re-suspended in complete media (5 mL) counted and adjusted to a concentration of $3.125\times10^4$ cells/mL before being added to the 384 well assay plate (Corning #3701) at 40 μL per well. The cells were left for a minimum of three hours, at 37° C./5% $CO_2$, to adhere to the plate.

Compounds were serially diluted in DMSO before receiving an aqueous dilution into a 384 well dilution plate (Greiner #781281), where 5 μL from the titration plate was transferred to 45 μL of complete media and mixed to give a solution containing 10% DMSO.

Mixtures of TNFα and IL-17 cytokine were prepared in complete media to final concentrations of TNFα 25 pM/IL-17A 50 pM, then 30 μL of the solution was added to a 384 well reagent plate (Greiner #781281).

10 μL from the aqueous dilution plate was transferred to the reagent plate containing 30 μL of the diluted cytokines, to give a 2.5% DMSO solution. The compounds were incubated with the cytokine mixtures for 5 h at 37° C. After the incubation, 10 μL was transferred to the assay plate, to give a 0.5% DMSO solution, then incubated for 18-20 h at 37° C./5% $CO_2$.

From the Cisbio IL-6 FRET kit (Cisbio #62IL6PEB) europium cryptate and Alexa 665 were diluted in reconstitution buffer and mixed 1:1, as per kit insert. To a white low volume 384 well plate (Greiner #784075) were added FRET reagents (10 μL), then supernatant (10 μL) was transferred from the assay plate to Greiner reagent plate. The mixture was incubated at room temperature for 3 h with gentle shaking (<400 rpm) before being read on a Synergy Neo 2 plate reader (Excitation: 330 nm; Emission: 615/645 nm).

When tested in the HDF cell line assay as described above, the compounds of the accompanying Examples were found to exhibit the following $pIC_{50}$ values.

| Example | $pIC_{50}$ |
|---|---|
| 1 | 7.2 |
| 2 | 7.2 |
| 3 | 4.8 |
| 4 | 5.5 |
| 5 | 6.4 |
| 6 | 7.9 |
| 7 | 5.6 |
| 8 | 8.1 |
| 9 | <5.0 |
| 10 | 5.0 |
| 11 | 8.3 |
| 12 | 6.1 |

The following Examples illustrate the preparation of compounds according to the invention.

EXAMPLES

| Abbreviations | |
|---|---|
| DCM: dichloromethane | EtOAc: ethyl acetate |
| MeOH: methanol | THF: tetrahydrofuran |
| DMSO: dimethyl sulfoxide | DIPEA: N,N-diisopropylethylamine |
| EtOH: ethanol | DMF: N,N-dimethylformamide |
| TFA: trifluoroacetic acid | DBU: 1,8-diazabicyclo[5.4.0]undec-7-ene |
| TBAF: tetrabutylammonium fluoride | IPA: isopropanol |
| DMPU: 1,3-dimethyl-3,4,5,6-tetrahydro-2(1H)-pyrimidinone | |
| T3P ®: propylphosphonic anhydride solution | |
| HATU: 1-[bis(dimethylamino)methylene]-1H-1,2,3-triazolo[4,5-b]pyridinium 3-oxid hexafluorophosphate | |
| $NiCl_2$ glyme: nickel(II) chloride ethylene glycol dimethyl ether complex | |
| $\{Ir[dF(CF_3)ppy]_2(dtbpy)\}PF_6$: [4,4'-bis(1,1-dimethylethyl)-2,2'-bipyridine-N1,N1']bis-{3,5-difluoro-2-[5-(trifluoromethyl)-2-pyridinyl-N]phenyl-C}iridium(III) hexafluorophosphate | |
| h: hour | r.t.: room temperature |
| M: mass | RT: retention time |
| HPLC: High Performance Liquid Chromatography | |
| LCMS: Liquid Chromatography Mass Spectrometry | |
| SFC: Supercritical Fluid Chromatography | |

Analytical Conditions

Method 1

Short pH 3.

Stationary Phase: Phenomenex Gemini NX-C18 (2×20 mm, 3 m column)

Mobile Phase A: 10 mM ammonium formate in water+0.1% formic acid

Mobile Phase B: acetonitrile+5% water+0.1% formic acid

Flow rate: 1 mL/minute

Gradient Program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 2

Short pH 10.

Stationary Phase: Phenomenex Gemini NX-C18 (2×20 mm, 3 m column)

Mobile Phase A: 10 mM ammonium formate in water+0.1% ammonia solution

Mobile Phase B: acetonitrile+5% water+0.1% ammonia solution

Flow rate: 1 mL/minute

Gradient Program:

| Time | A % | B % |
|---|---|---|
| 0.00 | 95.00 | 5.00 |
| 1.50 | 5.00 | 95.00 |
| 2.25 | 5.00 | 95.00 |
| 2.50 | 95.00 | 5.00 |

Method 3

Long pH 10.

Stationary Phase: Phenomenex Gemini NX-C18 (2×20 mm, 3 m column)

Mobile Phase A: 10 mM ammonium formate in water+0.1% ammonia solution

Mobile Phase B: acetonitrile+5% water+0.1% ammonia solution

Flow rate: 1 mL/minute

Gradient Program:

| Time | A % | B % |
|---|---|---|
| 0.00 | 95.00 | 5.00 |
| 4.00 | 5.00 | 95.00 |
| 5.00 | 5.00 | 95.00 |
| 5.10 | 95.00 | 5.00 |

Method 4

Purification on a Waters AP fractionlynx system, in tandem with a Waters SQD2 mass spectrometer.

Stationary Phase: Waters Xbridge Prep C18 OBD (19×100 mm, 5 μm column)

Column Temperature: Ambient

Mobile Phase A: 10 mM ammonium bicarbonate in water+0.1% ammonia solution

Mobile Phase B: acetonitrile+5% water+0.1% ammonia solution

Flow rate: 19 mL/minute

Gradient program: Focused gradient 35-50% mobile phase B in mobile phase A with run time of 13 minutes Method 5

MSDXT, pH 10.

Stationary Phase: Waters Acquity UPLC BEH C18 (2.1×50 mm, 1.7 m column)

Mobile Phase A: 10 mM ammonium formate in water+0.1% ammonia solution

Mobile Phase B: acetonitrile+5% water+0.1% ammonia solution

Flow rate: 1.5 mL/minute

Gradient Program:

| Time | A % | B % |
|---|---|---|
| 0.00 | 95.00 | 5.00 |
| 0.10 | 95.00 | 5.00 |
| 3.50 | 5.00 | 95.00 |
| 4.00 | 5.00 | 95.00 |
| 4.05 | 95.00 | 5.00 |

Method 6

Purification on a Waters AP fractionlynx System, in tandem with a Waters 3100 mass spectrometer.

Stationary Phase: Waters Xbridge Prep C18 OBD (19×150 mm, 5 μm column)

Column Temperature: Ambient

Mobile Phase A: 10 mM ammonium bicarbonate in water+0.1% ammonia solution

Mobile Phase B: acetonitrile+5% water+0.1% ammonia solution

Flow rate: 19 mL/minute

Gradient program: Focused gradient 45-60% mobile phase B in mobile phase A with run time of 13 minutes Method 7

Chiral purification carried out by SFC on a Waters Prep 100 fractionlynx system, in tandem with a Waters SQD2 mass spectrometer.

Stationary Phase: Lux Cellulose-4 (250×21.2 mm, 5 μm column)

Flow rate: 100 mL/minute

ABPR: 60 bar

Mobile Phase: Gradient of 5-25% MeOH (+0.1% $NH_4OH$)

Column Temperature: 40° C.

Run time: 7.5 minutes

Method 8

Chiral purification carried out by SFC on a Waters Prep 150 fractionlynx system, in tandem with a Waters QDa mass spectrometer.

Stationary Phase: Lux Cellulose-1 (250×21.2 mm, 5 μm column)

Flow rate: 100 mL/minute

ABPR: 60 bar

Mobile Phase: Gradient of 3-40% MeOH (+0.1% $NH_4OH$)

Column Temperature: 40° C.

Run time: 7.5 minutes

Method 9

Chiral analysis carried out on a Waters Prep 100 fractionlynx system, in tandem with a Waters SQD2 mass spectrometer.

Stationary Phase: Lux Cellulose-1 (150×4.6 mm, 3 μm column)

Flow rate: 3 mL/minute

Mobile Phase: 3-40% MeOH (+0.1% $NH_4OH$)

Column Temperature: 35° C.

Run time: 6.5 minutes

Method 10

Chiral analysis carried out on a Waters Prep 100 fractionlynx system, in tandem with a Waters SQD2 mass spectrometer.

Stationary Phase: Lux Cellulose-4 (150×4.6 mm, 3 μm column)

Flow rate: 3 mL/minute

Mobile Phase: 3-40% MeOH (+0.1% $NH_4OH$)

Column Temperature: 35° C.

Run time: 6.5 minutes

Method 11

Chiral purification carried out on a Waters Prep 150 fractionlynx system, in tandem with a Waters QDa mass spectrometer.

Stationary Phase: Lux Cellulose-4 (250×21.2 mm, 5 μm column)
Flow rate: 100 mL/minute
Mobile Phase: Gradient of 3-25% MeOH (+0.1% $NH_4OH$)
Column Temperature: 40° C.
Run time: 10 minutes Method 12

Chiral purification carried out on a Waters Prep 150 fractionlynx system, in tandem with a Waters QDa mass spectrometer.

Stationary Phase: Chiralpak IH (250×20 mm, 5 μm column)
Flow rate: 100 mL/minute
Mobile Phase: Gradient of 3-25% MeOH (+0.1% $NH_4OH$)
Column Temperature: 40° C.
Run time: 10 minutes Method 13

Chiral analysis carried out on a Waters Prep 100 fractionlynx system, in tandem with a Waters SQD2 mass spectrometer.

Stationary Phase: Lux Cellulose-4 (150×4.6 mm, 5 μm column)
Flow rate: 3 mL/minute
Mobile Phase: Gradient of 3-40% MeOH (+0.1% $NH_4OH$)
Column Temperature: 35° C.
Run time: 6.5 minutes Method 14

Chiral analysis carried out on a Waters Prep 100 fractionlynx system, in tandem with a Waters SQD2 mass spectrometer.

Stationary Phase: Chiralpak IH (150×4.6 mm, 3 μm column)
Flow rate: 3 mL/minute
Mobile Phase: Gradient of 3-25% MeOH (+0.1% $NH_4OH$)
Column Temperature: 35° C.
Run time: 6.5 minutes Method 15

Stationary Phase: Chiralpak AD-3, 100×6.4 mm, 3 μm
Column Temperature: 35° C.
Mobile Phase A: $C_{02}$
Mobile Phase B: IPA (0.05% IP Am)
Flow rate: 3.4 mL/minute
Gradient program:

| Time | A % | B % |
|---|---|---|
| 0.00 | 95 | 5 |
| 2.00 | 60 | 40 |
| 3.00 | 60 | 40 |
| 3.60 | 95 | 5 |
| 4.00 | 95 | 5 |

Method 16

Chiral analysis was performed using a (R,R) Whelk-O1 150×4.6 mm, 5 μm column, flow rate 3 mL/minute, column temperature 35° C., eluting with a gradient 3-40% MeOH (+0.1% $NH_4OH$) method (ABPR 120 bar), using a 6.5 minute run time on a Waters UPC$^2$ Acquity system, in tandem with a Waters QDa mass spectrometer.

Intermediate 1 tert-Butyl N-(2-amino-6-bromopyridin-3-yl)carbamate

To a solution of 6-bromopyridine-2,3-diamine (100 g, 521 mmol) and di-tert-butyl dicarbonate (126.5 g, 574 mmol) in EtOH (550 mL) at r.t. was added guanidine hydrochloride (5.60 g, 58.0 mmol). The mixture was heated to 50° C., resulting in effervescence (which subsided after approximately 4 h). The mixture was stirred at 50° C. for 21 h, then cooled to r.t. The precipitate was filtered, washed sequentially with EtOH (100 mL) and isohexane (300 mL), then dried, to give the title compound (140.6 g, 94%) as a tan-coloured powder. $\delta_H$ (300 MHz, DMSO-$d_6$) 8.45 (s, 1H), 7.55 (d, J 8.1 Hz, 1H), 6.69 (d, J 8.0 Hz, 1H), 6.24 (s, 2H), 1.46 (s, 9H).

Intermediate 2

2-Amino-3,3-dicyclopropylpropanoic acid hydrochloride 2,2-Dicyclopropylacetaldehyde (5.00 g, 40.3 mmol) in THE (16 mL) was added to a suspension of ammonium carbonate (9.67 g, 101 mmol) and potassium cyanide (3.28 g, 50.4 mmol) in water (16 mL) in a sealed pressure flask. The mixture was heated at 60° C. for 18 h, then cooled using an ice bath. Aqueous hydrochloric acid (6M) was added carefully to adjust the pH to <5. The resultant white solid was filtered, washed with water and dried in vacuo. The resulting crude 5-(dicyclopropylmethyl)imidazolidine-2,4-dione (colourless solid) (6.42 g) was suspended in aqueous NaOH solution (5M, 45 mL) and heated at reflux temperature for 18 h. The mixture was cooled to room temperature, then placed in an ice bath and acidified with concentrated aqueous hydrochloric acid (20 mL) to adjust the pH<5, whereupon a precipitate formed. The mixture was extracted with EtOAc (100 mL, then 30 mL). The aqueous layer was concentrated in vacuo and freeze-dried (acetonitrile/water), then extracted with warm ethanol (100 mL) and filtered. The ethanol layer was concentrated in vacuo to give the title compound (containing 15% w/w $NH_4Cl$) (3.5 g, 51%) as a light pink solid. $\delta_H$ (400 MHz, $D_2O$) 4.01 (d, J 3.5 Hz, 1H), 0.89-0.65 (m, 3H), 0.65-0.22 (m, 6H), 0.22-0.04 (m, 2H).

Intermediate 3

2-(Benzyloxycarbonylamino)-3,3-dicyclopropylpropanoic acid

To a suspension of Intermediate 2 (2.5 g, 12.0 mmol) and triethylamine (5.9 mL, 42 mmol) in DCM (60 mL) at 0° C. (cooled in an ice/water bath) was added N-(benzyloxycarbonyloxy)succinimide (2.9 g, 11.4 mmol) in portions. The reaction mixture was stirred at r.t. for 21 h, then diluted and washed with aqueous hydrochloric acid solution (1M, 3×50 mL). The resulting mixture was passed through a phase separator and concentrated in vacuo. The crude residue was re-dissolved in DCM (50 mL), then aqueous NaOH solution (1M, 50 mL) was added and the layers were separated. DCM (50 mL) and aqueous hydrochloric acid (2M, 50 mL) were added to the basic aqueous layer, then the layers were separated and the aqueous layer was re-extracted with DCM (2×30 mL). The combined DCM layers were passed through a phase separator and concentrated in vacuo to give the crude title compound (90% purity) (1.69 g, 46%) as a yellow oil, which was utilised without further purification. $\delta_H$ (400 MHz, DMSO-$d_6$) 12.53 (s, 1H), 7.48 (d, J 8.9 Hz, 1H), 7.42-7.28 (m, 5H), 5.09 (d, J 12.7 Hz, 1H), 5.04 (d, J 12.7 Hz, 1H), 4.20 (dd, J 8.9 and 4.4 Hz, 1H), 1.06-0.91 (m, 1H), 0.85-0.74 (m, 1H), 0.58-0.43 (m, 2H), 0.42-0.21 (m, 4H), 0.20-0.00 (m, 3H). LCMS (Method 1): $[M+H]^+$ m/z 304.0, RT 1.18 minutes.

Intermediate 4 tert-Butyl N-(2-{[2-(benzyloxycarbonylamino)-3,3-dicyclopropylpropanoyl]amino}-6-bromopyridin-3-yl)carbamate T3P® (50 mass % in EtOAc, 9.7 mL, 16 mmol) was added dropwise to a solution of Intermediate 1 (1.90 g, 6.59 mmol), Intermediate 3 (2.00 g, 6.59 mmol) and pyridine (99.8 mass %, 2.4 mL, 30 mmol) in EtOAc (19.8 mL) at 0° C. The ice bath was removed and the reaction mixture was stirred at r.t. for 21.5 h, then diluted with EtOAc (20 mL) and washed with water (50 mL, then 2×30 mL). The combined aqueous layers were extracted with EtOAc (2×30 mL). The combined organic layers were washed with saturated aqueous $NaHCO_3$ solution (50 mL) and brine (50 mL), then passed through a phase separator and concentrated in vacuo. The crude residue was purified by flash column chromatography, eluting with a gradient of 0-30% EtOAc in hexanes, to give the title compound (2.59 g, 68%) as a white solid. $\delta_H$ (400 MHz, DMSO-$d_6$) 10.92 (s, 1H), 8.24 (s, 1H), 8.05 (d, J 8.5 Hz, 1H), 7.66 (d, J 8.5 Hz, 1H), 7.54 (d, J 8.5 Hz, 1H), 7.41-7.23 (m, 5H), 5.07 (s, 2H), 4.55 (dd, J 8.5, 5.5 Hz, 1H), 1.43 (s, 9H), 1.08-0.93 (m, 1H), 0.90-0.78 (m, 1H), 0.60 (td, J 9.6, 5.6 Hz, 1H), 0.54-0.46 (m, 1H), 0.42-0.15 (m, 7H). LCMS (Method 2): $[M+H]^+$ m/z 573.0, 574.8, RT 1.68 minutes.

Intermediate 5

Benzyl N-[1-(5-bromo-1H-imidazo[4,5-b]pyridin-2-yl)-2,2-dicyclopropylethyl]carbamate TFA (3.4 mL, 45 mmol) was added dropwise to a solution of Intermediate 4 (2.58 g, 4.50 mmol) in DCM (13.5 mL) at r.t. under nitrogen. The reaction mixture was stirred at 40° C. for 4 h, then diluted with DCM (30 mL) and washed with saturated aqueous $NaHCO_3$ solution (150 mL). The aqueous layer was extracted with DCM (2×30 mL), and the combined organic layers were passed through a phase separator and concentrated in vacuo. The crude residue was purified by flash column chromatography, eluting with a gradient of 0-50% EtOAc in hexanes, to give the title compound (1.81 g, 88%) as a white solid. $\delta_H$ (400 MHz, $CDCl_3$) 7.82 (s, 1H), 7.39 (d, J 8.3 Hz, 1H), 7.37-7.30 (m, 5H), 6.48 (br s, 1H), 5.22 (t, J 7.2 Hz, 1H), 5.16 (d, J 12.3 Hz, 1H), 5.11 (d, J 12.3 Hz, 1H), 1.17-1.04 (m, 1H), 0.88-0.74 (m, 2H), 0.56-0.45 (m, 2H), 0.43-0.32 (m, 2H), 0.32-0.19 (m, 2H), 0.18-0.10 (m, 1H), 0.06 to −0.05 (m, 1H). One of the NH proton signals was not visible. LCMS (Method 3): $[M+H]^+$ m/z 454.8, 456.8, RT 2.48 minutes.

Intermediate 6

Mixture of benzyl N-{1-[5-bromo-1-(2-trimethylsilylethoxymethyl)imidazo[4,5-b]-pyridin-2-yl]-2,2-dicyclopropylethyl}carbamate and benzyl N-{1-[5-bromo-3-(2-trimethylsilylethoxymethyl)imidazo[4,5-b]pyridin-2-yl]-2,2-dicyclopropylethyl}-carbamate 2-(Trimethylsilyl)ethoxymethyl chloride (0.96 mL, 5.2 mmol), followed by $K_2CO_3$ (715 mg, 5.17 mmol), were added to a solution of Intermediate 5 (100 mass %, 1.8125 g, 3.980 mmol) in DMF (20 mL) under nitrogen. The reaction mixture was stirred at r.t. for 6.5 h, then diluted with EtOAc (50 mL) and washed with water (3×50 mL). The combined aqueous layers were extracted with EtOAc (2×20 mL), then the combined organic layers were washed with brine (50 mL), passed through a phase separator and concentrated in vacuo. The crude residue was purified by flash column chromatography, eluting with a gradient of 0-50% EtOAc in hexanes, to give a mixture of the title compounds (2.32 g, 99%) as a colourless oil. LCMS (Method 2): $[M+H]^+$ m/z 585.0, 587.0, RT 1.82 minutes (isomer 1); and m/z 585.0, 587.0, RT 1.92 minutes (isomer 2).

Intermediate 7 tert-Butyl 2-{2-[1-(benzyloxycarbonylamino)-2,2-dicyclopropylethyl]-1-(2-trimethyl-silylethoxymethyl)imidazo[4,5-b]pyridin-5-yl}-4,4-difluoropiperidine-1-carboxylate tert-Butyl 2-{2-[1-(benzyloxycarbonylamino)-2,2-dicyclopropylethyl]-3-(2-trimethyl-silylethoxymethyl)imidazo[4,5-b]pyridin-5-yl}-4,4-difluoropiperidine-1-carboxylate DBU (0.45 mL, 3.0 mmol) was added to a 40 mL screw-cap vial containing Intermediate 6 (1.16 g, 1.98 mmol), 1-tert-butoxycarbonyl-4,4-difluoropiperidine-2-carboxylic acid (1.05 g, 3.96 mmol), $\{Ir[dF(CF_3)ppy]_2(dtbpy)\}PF_6$ (22.2 mg, 0.020 mmol), $NiCl_2$ glyme (66.6 mg, 0.297 mmol) and 4,4'-di-tert-butyl-2,2'-dipyridyl (81.3 mg, 0.297 mmol) in DMF (28.3 mL). The vial was sealed, and nitrogen was bubbled through the solution for 10 minutes. The vial lid was quickly replaced with an unpierced lid, and the joint was sealed with parafilm. The reaction vessel was irradiated (450 nm) using a photoreactor (*ACS Cent. Sci.*, 2017, 3, 647-653) (settings: Fan, 1800 rpm; Stir, 250 rpm; LED, 100%) for 16 h. An identical procedure was performed simultaneously in parallel. The two parallel reaction mixtures were combined, then diluted with EtOAc (50 mL) and washed with water (3×50 mL). The combined aqueous layers were extracted with EtOAc (2×30 mL). The combined organic layers were washed with brine (50 mL), passed through a phase separator and concentrated in vacuo. The crude residue was purified by flash column chromatography, eluting with a gradient of 0-100% EtOAc in hexanes, to give a mixture of the title compounds (2.72 g, 95%) as a pale yellow foam. LCMS (Method 2): $[M+H]^+$ m/z 726.0, RT 1.92 minutes (isomer 1); and m/z 726.0, RT 1.99 minutes (isomer 2).

Intermediate 8

Benzyl N-{2,2-dicyclopropyl-1-[5-(4,4-difluoropiperidin-2-yl)-1H-imidazo[4,5-b]pyridin-2-yl]ethyl}carbamate TFA (2.8 mL, 37 mmol) was added dropwise to a solution of Intermediate 7 (2.71 g, 3.74 mmol) in DCM (11.2 mL)

under nitrogen. The reaction mixture was stirred at r.t. for 17.5 h, then diluted with DCM (20 mL), poured into saturated aqueous $NaHCO_3$ solution (150 mL) and stirred for 10 minutes. The layers were separated, and the aqueous layer was extracted with DCM (2×30 mL). The combined organic layers were passed through a phase separator and concentrated in vacuo. The crude residue was purified by flash column chromatography, eluting with a gradient of 0-100% EtOAc in hexanes, then 0-20% MeOH in EtOAc, to give the title compound (0.458 g, 25%) as a pale yellow solid and a by-product (1.11 g) as a yellow oil. The by-product was taken up in DCM (35.5 mL), and TFA (6.7 mL, 89 mmol) was added dropwise under nitrogen. The reaction mixture was stirred at r.t. for 23 h, then concentrated in vacuo, diluted with DCM (40 mL), poured into saturated aqueous $NaHCO_3$ solution (100 mL) and stirred for 10 minutes. The layers were separated, and the aqueous layer was extracted with DCM (2×30 mL). The combined organic layers were passed through a phase separator and concentrated in vacuo. The crude residue was purified by flash column chromatography, eluting with a gradient of 0-100% EtOAc in hexanes, then 0-10% MeOH in EtOAc, to give additional title compound (0.872 g, 47%) (combined yield from both batches of 1.33 g, 72%) as a pale yellow foam. LCMS (Method 2): $[M+H]^+$ m/z 496.0, RT 1.37 minutes.

Intermediate 9

Benzyl N-(2,2-dicyclopropyl-1-{5-[4,4-difluoro-1-(3-fluorobicyclo[1.1.1]pentane-1-carbonyl)piperidin-2-yl]-1H-imidazo[4,5-b]pyridin-2-yl}ethyl)carbamate HATU (1.16 g, 2.95 mmol), followed by DIPEA (1.4 mL, 8.1 mmol), were added to a solution of Intermediate 8 (1.33 g, 2.68 mmol) and 3-fluorobicyclo[1.1.1]pentane-1-carboxylic acid (404 mg, 2.95 mmol) in DMF (40 mL). The reaction mixture was stirred at r.t. for 1.5 h, then diluted with EtOAc (50 mL) and washed with water (4×50 mL). The combined aqueous layers were extracted with EtOAc (2×40 mL). The combined organic layers were washed with brine (50 mL), passed through a phase separator and concentrated in vacuo. The crude residue was purified by flash column chromatography, eluting with a gradient of 0-100% EtOAc in hexanes, then 0-20% MeOH in EtOAc, to give the title compound (0.923 g, 57%) as a pale yellow foam. LCMS (Method 2): $[M+H]^+$ m/z 608.0, RT 1.48 minutes.

Intermediate 10

{2-[2-(1-Amino-2,2-dicyclopropylethyl)-1H-imidazo[4,5-b]pyridin-5-yl]-4,4-difluoro-piperidin-1-yl}(3-fluorobicyclo[1.1.1]pentan-1-yl)methanone Palladium on carbon (10 mass %, 323 mg, 0.304 mmol) was added to a solution of Intermediate 9 (0.923 g, 1.52 mmol) in EtOH (15.2 mL). The reaction mixture was evacuated and placed under an atmosphere of hydrogen, then stirred at r.t. for 2.5 h. The reaction mixture was filtered through a pad of Celite®, washed through with EtOH (2×30 mL) and concentrated in vacuo. The residue was concentrated in vacuo from EtOAc an additional three times, to give the title compound (0.694 g, 97%) as a grey foam, which was utilised without further purification. LCMS (Method 2): $[M+H]^+$ m/z 474.0, RT 1.23 minutes.

Intermediate 11

$N^2$,$N^2$,$N^3$,$N^3$-Tetrabenzyl-6-bromopyridine-2,3-diamine

To a solution of 6-bromopyridine-2,3-diamine (4.0 g, 21.27 mmol) in DMF (80 mL) at r.t. was added NaH (10.2 g, 255 mmol) portionwise. The mixture was stirred for 30 minutes at r.t., then placed in an ice bath. Benzyl bromide (23.2 mL, 191 mmol) was cautiously added dropwise via syringe over a period of 25 minutes. The reaction mixture was left to stir at r.t. overnight, then thoroughly agitated whilst water (100 mL) was added dropwise, very slowly. The reaction mixture was further diluted with EtOAc (200 mL), and the layers were separated. The organic phase washed twice with water. The combined organic phases were dried, filtered and concentrated in vacuo. Purification by flash column chromatography on silica (Biotage SNAP 340 g, Isolera), eluting with 0-60% toluene/hexane, yielded the title compound (8.21 g, 70%) as a transparent, pale yellow semi-solid. LCMS (Method 2): $[M+H]^+$ m/z 548.0, 550.0, RT 1.97 minutes.

Intermediate 12 tert-Butyl 2-[5,6-bis(dibenzylamino)pyridin-2-yl]-4-oxopiperidine-1-carboxylate

To a solution of Intermediate 11 (8.30 g, 15.0 mmol) in THE (80 mL) at −78° C. was added n-butyllithium (7.20 mL, 18.0 mmol) dropwise over 10 minutes. The orange material was stirred at −78° C. for 20 minutes, then CuI (1.40 g, 7.30 mmol) was added in three portions at −78° C. The reaction mixture was immediately warmed to 0° C. and stirred for 20 minutes, then re-cooled to −78° C. A mixture of tert-butyl 4-oxo-2,3-dihydropyridine-1-carboxylate (1.10 g, 5.60 mmol) and chlorotrimethylsilane (5.80 mL, 45.0 mmol) in THE (28 mL) (pre-stirred at r.t. for 5 minutes) was added via cannula over 10 minutes, and rinsed with THE (2×5 mL). The resulting brown mixture was allowed to warm gradually to r.t. After 4 h, the mixture was quenched with TBAF (1M in THF, 20 mL) at r.t, then stirred for 5 minutes and diluted with water (20 mL). The mixture was extracted with EtOAc (3×100 mL), and the combined organic layers were dried over $MgSO_4$ and concentrated in vacuo. Purification by flash chromatography, eluting with EtOAc/isohexane (0-100% gradient), gave the title compound (3.60 g, 97%) as a beige solid. $\delta_H$ (400 MHz, 373K, DMSO-$d_6$) 7.24-7.15 (m, 12H), 7.12 (d, J 8.0 Hz, 1H), 7.11-7.05 (m, 8H), 6.70 (d, J 7.9 Hz, 1H), 5.41 (unresolved dd, J 5.3, 4.3 Hz, 1H), 4.79 (d, J 15.0 Hz, 2H), 4.63 (d, J 15.0 Hz, 2H), 4.37 (d, J 14.3 Hz, 2H), 4.31 (d, J 14.3 Hz, 2H), 3.88 (dddd, J 13.4, 6.7, 4.4, 1.1 Hz, 1H), 3.11 (ddd, J 13.2, 9.8, 4.7 Hz, 1H), 2.74-2.63 (m, 2H), 2.35 (ddd, J 16.4, 9.8, 6.7 Hz, 1H), 2.15 (dt, J 16.4, 4.5 Hz, 1H), 1.40 (s, 9H). LCMS (Method 2): $[M+H]^+$ m/z 667, RT 1.94 minutes.

Intermediates 13 & 14 syn-(rac)-tert-Butyl 2-[5,6-bis(dibenzylamino)pyridin-2-yl]-4-hydroxy-4-(trifluoro-methyl)piperidine-1-carboxylate (Intermediate 13)

Anti-(rac)-tert-Butyl 2-[5,6-bis(dibenzylamino)pyridin-2-yl]-4-hydroxy-4-(trifluoro-methyl)piperidine-1-carboxylate (Intermediate 14)

To a solution of Intermediate 12 (10.0 g, 15.0 mmol) in THE (30 mL) at −5° C. was added (trifluoromethyl)trimethylsilane (9.53 mL, 60.0 mmol) dropwise via syringe. TBAF (1M in THF, 60.0 mL, 60.0 mmol) was subsequently added via syringe over 15 minutes. The mixture was warmed to r.t. over 60 h, then quenched by the addition of saturated aqueous $NaHCO_3$ solution (75 mL) and diluted with EtOAc (200 mL). The layers were separated, and the aqueous layer was re-extracted with EtOAc (2×200 mL). The combined organic layers were dried ($Na_2SO_4$) and concentrated in vacuo.

Purification by flash chromatography, eluting with EtOAc/isohexane (0-30% gradient), gave Intermediate 13 (6.67 g, 60%) and Intermediate 14 (2.80 g, 25%) as yellow foams.

Intermediate 13: $\delta_H$ (400 MHz, 373K, DMSO-$d_6$) 7.25-7.16 (m, 12H), 7.15-7.10 (m, 5H), 7.08-6.96 (m, 4H), 6.68 (d, J 8.0 Hz, 1H), 5.83 (s, 1H, OH), 5.23 (d, J 6.9 Hz, 1H), 4.81 (d, J 14.8 Hz, 2H), 4.71 (d, J 14.9 Hz, 2H), 4.35 (d, J 14.3 Hz, 2H), 4.28 (d, J 14.3 Hz, 2H), 3.95 (dt, J 13.5, 3.8 Hz, 1H), 3.21-3.08 (m, 1H), 2.56-2.45 (obscured m, 1H), 2.02 (dd, J 14.2, 7.3 Hz, 1H), 1.72-1.66 (m, 2H), 1.37 (s, 9H). LCMS (Method 2): $[M+H]^+$ m/z 737, RT 2.03 minutes.

Intermediate 14: $\delta_H$ (400 MHz, 373K, DMSO-$d_6$) 7.22-7.11 (m, 16H), 7.06 (m, 5H), 6.60 (d, J 8.0 Hz, 1H), 5.70 (br s, 1H, OH), 4.84 (t, J 8.3 Hz, 1H), 4.79 (d, J 14.7 Hz, 2H), 4.73 (d, J 14.7 Hz, 2H), 4.33 (d, J 14.3 Hz, 2H), 4.31 (d, J 14.3 Hz, 2H), 3.89 (ddd, J 13.6, 6.6, 3.9 Hz, 1H), 3.23 (ddd, J 13.6, 10.2, 5.4 Hz, 1H), 2.56-2.47 (obscured m, 1H), 2.00 (br s, 1H), 1.89 (ddd, J 14.4, 5.4, 3.9 Hz, 1H), 1.82-1.61 (m, 1H), 1.24 (s, 9H). LCMS (Method 2): $[M+H]^+$ m/z 737, RT 1.94 minutes.

Intermediate 15 syn-(rac)-tert-Butyl-2-(5,6-diaminopyridin-2-yl)-4-hydroxy-4-(trifluoromethyl)-piperidine-1-carboxylate To a solution of Intermediate 13 (6.58 g, 8.93 mmol) in MeOH (150 mL) at r.t. was added 12N aqueous HCl (1.64 mL, 19.7 mmol), followed by 10% Pd/C (1.65 g), portion-wise. The vessel was evacuated and purged with $H_2$, then left to stir at r.t. for 3 days. The mixture was filtered through a pad of Celite® under suction, washing through with EtOH, then concentrated in vacuo. Purification by flash chromatography, eluting with EtOAc/isohexane (0-100% gradient), then MeOH/DCM (10% gradient), gave the title compound (7.3:1 ratio of debenzylated and mono-benzylated material) (2.00 g, 60%) as a brown foam. $\delta_H$ (400 MHz, 373K, DMSO-$d_6$) 6.80 (d, J 7.6 Hz, 1H), 6.50 (d, J 7.6 Hz, 1H), 5.43 (br s, 2H), 5.34 (app d, J 7.5 Hz, 1H), 4.65 (br s, 2H), 3.92 (dt, J 13.6, 3.3 Hz, 1H), 3.09 (ddd, J 13.7, 10.0, 5.5 Hz, 1H), 2.16 (d, J 14.2 Hz, 1H), 2.06 (dd, J 14.3, 7.5 Hz, 1H), 1.70-1.62 (m, 2H), 1.44 (s, 9H). The OH proton signal was not observed. LCMS (Method 2): $[M+H]^+$ m/z 377, RT 1.25 minutes.

Intermediate 16 syn-(rac)-tert-Butyl-2-[6-amino-5-(tert-butoxycarbonylamino)pyridin-2-yl]-4-hydroxy-4-(trifluoromethyl)piperidine-1-carboxylate To a solution of Intermediate 15 (2.00 g, 5.31 mmol) in EtOH (20 mL) was added di-tert-butyl dicarbonate (1.40 mL. 6.00 mmol), followed by guanidine hydrochloride (77 mg, 0.80 mmol) in one portion. A reflux condenser was fitted, and the mixture was stirred at 50° C. for 16 h, then cooled to r.t. and concentrated in vacuo. Purification by flash chromatography, eluting with EtOAc/isohexane (0-100% gradient), gave the title compound (934 mg, 37%) as a pale yellow foam. $\delta_H$ (400 MHz, 373K, DMSO-$d_6$) 8.16 (s, 1H), 7.63 (d, J 7.9 Hz, 1H), 7.52 (s, 1H), 6.59 (dd, J 7.8, 0.6 Hz, 1H), 5.70 (s, 2H), 5.34 (d, J 7.4 Hz, 1H), 3.97 (dt, J 13.5, 3.3 Hz, 1H), 3.14 (ddd, J 13.7, 9.2, 6.3 Hz, 1H), 2.36-2.29 (m, 1H), 2.06 (dd, J 14.3, 7.6 Hz, 1H), 1.73-1.66 (m, 2H), 1.49 (s, 9H), 1.44 (s, 9H). LCMS (Method 2): $[M+H]^+$ m/z 477, RT 1.46 minutes.

Intermediate 17 syn-(rac)-tert-Butyl-2-[6-{[2-(benzyloxycarbonylamino)-3,3-dicyclopropylpropanoyl]-amino}-5-(tert-butoxycarbonylamino)pyridin-2-yl]-4-hydroxy-4-(trifluoromethyl)-piperidine-1-carboxylate To a solution of Intermediate 16 (372 mg, 0.78 mmol), Intermediate 3 (260 mg, 0.86 mmol) and pyridine (0.29 mL, 3.60 mmol) in EtOAc (2.2 mL) at 0° C. was added T3P® (50% wt in EtOAc, 1.15 mL, 1.95 mmol) dropwise over 2 minutes. The mixture was allowed to warm to r.t. and stirred for 20 h, then quenched by the addition of water (5 mL) and diluted with EtOAc (10 mL). The layers were separated, and the aqueous layer was re-extracted with EtOAc (3×10 mL). The combined organic layers were washed with saturated aqueous $NaHCO_3$ solution (20 mL), dried ($Na_2SO_4$) and concentrated in vacuo. Purification by flash chromatography, eluting with EtOAc/isohexane (0-100% gradient), gave the title compound (400 mg, 67%) as a white solid. LCMS (Method 2): $[M+H]^+$ m/z 762, RT 1.80 minutes.

Intermediate 18 syn-(rac)-Benzyl N-(2,2-dicyclopropyl-1-{5-[4-hydroxy-4-(trifluoromethyl)piperidin-2-yl]-1H-imidazo[4,5-b]pyridin-2-yl}ethyl)carbamate trifluoroacetic acid salt Intermediate 17 (400 mg, 0.53 mmol) was dissolved in DCM (1.6 mL), and TFA (0.60 mL, 7.90 mmol) was added. The mixture was stirred at 40° C. for 20 h, then cooled to r.t., neutralised with saturated aqueous $NaHCO_3$ solution and diluted with EtOAc (10 mL). The layers were separated, and the aqueous layer was re-extracted with EtOAc (2×10 mL). The combined organic layers were dried over $Na_2SO_4$ and concentrated in vacuo to give the title compound (329 mg, 95%) as an orange foam. LCMS (Method 2): $[M+H]^+$ m/z 544, RT 1.28 minutes.

Intermediate 19 syn-(rac)-Benzyl N-(2,2-dicyclopropyl-1-{5-[I-(3-fluorobicyclo[1.1.1]pentane-1-carbonyl)-4-hydroxy-4-(trifluoromethyl)piperidin-2-yl]-1H-imidazo[4,5-b]pyridin-2-yl}-ethyl)carbamate To a solution of Intermediate 18 (mixture of four diastereomers) (329 mg, 0.50 mmol), 3-fluorobicyclo[1.1.1]pentane-1-carboxylic acid (72 mg, 0.55 mmol) and DIPEA (0.35 mL, 2.00 mmol) in DMF (10 mL) at r.t. was added HATU (236 mg, 0.60 mmol) in one portion. The mixture was stirred for 165 minutes, then water (10 mL) was added and the mixture was extracted with EtOAc (2×20 mL). The combined organic layers were washed with brine (20 mL), then dried ($Na_2SO_4$) and concentrated in vacuo. Purification by flash chromatography, eluting with EtOAc/isohexane (0-100% gradient), gave the title compound (298 mg, 91%) as a white foam. LCMS (Method 2): $[M+H]^+$ m/z 656, RT 1.47 minutes.

Intermediate 20 syn-(rac)-{2-[2-(1-Amino-2,2-dicyclopropylethyl)-1H-imidazo[4,5-b]pyridin-5-yl]-4-hydroxy-4-(trifluoromethyl)piperidin-1-yl}(3-fluorobicyclo[1.1.1]pentan-1-yl)methanone To a solution of Intermediate 19 (mixture of four diastereomers) (298 mg, 0.45 mmol) in EtOH (10 mL) at r.t. was added 10% Pd/C (30 mg). The vessel was evacuated and purged with $H_2$, then left to stir at r.t. for 40 minutes. The mixture was filtered through a pad of Celite® (10 g) under suction, washing through with EtOH (50 mL), then concentrated in vacuo, to give the title compound (237 mg, quantitative) as a grey foam, which was utilised without further purification. LCMS (Method 2): $[M+H]^+$ m/z 522, RT 1.24 minutes.

Intermediates 21 & 22 tert-Butyl (2S,4R)-2-[5,6-bis(dibenzylamino)pyridin-2-yl]-4-(difluoromethyl)-4-hydroxy-piperidine-1-carboxylate (syn diastereomer) (Intermediate 21)

tert-Butyl (2R,4R)-2-[5,6-bis(dibenzylamino)pyridin-2-yl]-4-(difluoromethyl)-4-hydroxy-piperidine-1-carboxylate (anti diastereomer) (Intermediate 22)

To a solution of Intermediate 12 (10.0 g, 15.0 mmol) and DMPU (9.25 mL) in THE (30 mL) at r.t. was added CsF (684 mg, 4.50 mmol) in one portion. The mixture was stirred for 5 minutes, then (difluoromethyl)trimethylsilane (4.09 mL, 30.0 mmol) was added dropwise over 2 minutes. Following the addition, the mixture was heated at 70° C. for 21 h, then cooled to r.t. TBAF (1M in THF, 15.0 mL, 15.0 mmol) was added and the mixture was stirred for 1 h, then poured into $H_2O$ (20 mL) and extracted with EtOAc (3×40 mL). The combined organic extracts were washed with $H_2O$ (2×30 mL), then dried ($Na_2SO_4$) and concentrated in vacuo. Purification by flash chromatography, eluting with EtOAc/isohexane (0-50% gradient), gave the racemic title compounds (Intermediate 21, 3.03 g, 28%; and Intermediate 22, 1.89 g, 17.5%) as yellow foams.

Intermediate 21: $\delta_H$ (400 MHz, 373K, DMSO-$d_6$) 7.25-7.16 (m, 12H), 7.16-7.10 (m, 5H), 7.10-7.04 (m, 4H), 6.68 (d, J 8.1 Hz, 1H), 5.65 (t, J 56.2 Hz, 1H), 5.23-5.17 (m, 1H), 5.08 (s, 1H), 4.79 (d, J 14.9 Hz, 2H), 4.73 (d, J 14.9 Hz, 2H), 4.34 (d, J 14.3 Hz, 2H), 4.29 (d, J 14.3 Hz, 2H), 3.90 (dt, J 13.5, 3.8 Hz, 1H), 3.15 (ddd, J 13.4, 11.9, 3.9 Hz, 1H), 2.33 (unresolved dt, J 14.4, 2.2 Hz, 1H), 1.91 (dd, J 14.2, 7.4 Hz, 1H), 1.64-1.45 (m, 2H), 1.36 (s, 9H). LCMS (Method 2): $[M+H]^+$ m/z 719.4, RT 2.00 minutes.

Intermediate 21: $\delta_H$ (400 MHz, 373K, DMSO-$d_6$) 7.27-7.10 (m, 17H), 7.09-7.01 (m, 4H), 6.58 (d, J 8.0 Hz, 1H), 5.46 (t, J 56.2 Hz, 1H), 4.98 (s, 1H), 4.87 (dd, J 8.8, 6.5 Hz, 1H), 4.81 (d, J 14.8 Hz, 2H), 4.74 (d, J 14.8 Hz, 2H), 4.34 (d, J 14.2 Hz, 2H), 4.30 (d, J 14.2 Hz, 2H), 3.87 (ddd, J 13.7, 6.2, 3.9 Hz, 1H), 3.17 (ddd, J 13.6, 10.6, 5.0 Hz, 1H), 2.02 (dd, J 14.0, 8.5 Hz, 1H), 1.86 (dd, J 14.2, 6.1 Hz, 1H), 1.80 (dt, J 14.5, 4.1 Hz, 1H), 1.66-1.55 (m, 1H), 1.25 (s, 9H). LCMS (Method 2): $[M+H]^+$ m/z 719.2, RT 1.93 minutes.

Intermediate 23 tert-Butyl (2S,4R)-2-(5,6-diaminopyridin-2-yl)-4-(difluoromethyl)-4-hydroxypiperidine-1-carboxylate To a solution of Intermediate 21 (4.76 g, 6.62 mmol) in MeOH (110 mL) at r.t. was added 12N aqueous HCl (1.21 mL, 14.5 mmol), followed by 10% Pd/C (1.17 g) portion-wise. The vessel was evacuated and purged with $H_2$, then left to stir at r.t. for 4 days. The mixture (58:42 desired: monobenzylated material) was filtered through a pad of Celite® under suction, washing through with MeOH (200 mL), then concentrated in vacuo. Purification by flash chromatography, eluting with EtOAc/isohexane (0-100% gradient), then MeOH/DCM (10% gradient), gave the title compound (605 mg, 25.5%) as a brown foam. $\delta_H$ (400 MHz, 373K, DMSO-$d_6$) 8.18 (s, 1H), 6.79 (d, J 7.6 Hz, 1H), 6.49 (d, J 7.6 Hz, 1H), 5.69 (t, J 56.3 Hz, 1H), 5.35 (br s, 2H), 5.31-5.26 (m, 1H), 4.59 (br s, 2H), 3.88 (dt, J 13.7, 3.5 Hz, 1H), 3.12 (ddd, J 13.5, 9.4, 6.2 Hz, 1H), 2.01 (obscured d, 1H), 1.93 (dd, J 14.3, 7.4 Hz, 1H), 1.56-1.50 (m, 2H), 1.43 (s, 9H). LCMS (Method 2): $[M+H]^+$ m/z 359.2, RT 1.16 minutes.

Intermediate 24 tert-Butyl (2S,4R)-2-[6-amino-5-(tert-butoxycarbonylamino)pyridin-2-yl]-4-(difluoromethyl)-4-hydroxypiperidine-1-carboxylate To a solution of Intermediate 23 (605 mg, 1.69 mmol) in EtOH (11.6 mL) was added di-tert-butyl dicarbonate (0.43 mL, 1.90 mmol), followed by guanidine hydrochloride (25 mg, 0.26 mmol) in one portion. A reflux condenser was fitted and the mixture was heated and stirred at 50° C. for 43 h, then cooled to r.t. and concentrated in vacuo. Purification by flash chromatography, eluting with EtOAc/isohexane (0-100% gradient), gave the title compound (710 mg, 92%) as a light brown foam. $\delta_H$ (400 MHz, 373K, DMSO-$d_6$) 8.15 (s, 1H), 7.61 (d, J 7.9 Hz, 1H), 6.78 (s, 1H), 6.58 (d, J 8.0 Hz, 1H), 5.70 (t, J 56.2 Hz, 1H), 5.64 (br s, 2H), 5.31-5.25 (m, 1H), 3.93 (dt, J 13.4, 3.8 Hz, 1H), 3.16 (ddd, J 13.5, 10.5, 5.2 Hz, 1H), 2.18 (unresolved dt, J 14.5, 1.9 Hz, 1H), 1.94 (dd, J 14.3, 7.5 Hz, 1H), 1.60-1.52 (m, 2H), 1.49 (s, 9H), 1.43 (s, 9H). LCMS (Method 2): $[M+H]^+$ m/z 459.2, RT 1.39 minutes.

Intermediates 25 & 26

(2S)-2-(Benzyloxycarbonylamino)-3,3-dicyclopropylpropanoic acid (Intermediate 25)

(2R)-2-(Benzyloxycarbonylamino)-3,3-dicyclopropyl propanoic acid (Intermediate 26)

Intermediate 3 (100% purity) (850 g, 2.80 mol) was subjected to separation by prep-SFC (column: Daicel Chiralpak AD, 250 mm×50 mm, 10 m; mobile phase: [Neu-IPA]; B %: 45%-45%, 6 minutes), and the fractions were concentrated in vacuo at 45° C., to provide the title compounds (Peak 1, 324 g, 1.07 mol, 100% purity; and Peak 2, 351 g, 1.16 mol, 100% purity) as white solids. $^1$H NMR and LCMS matched those for Intermediate 3. Chiral analysis (Method 15): Peak 1, RT 1.97 minutes; Peak 2, RT 2.29 minutes.

Intermediate 27 tert-Butyl (2S,4R)-2-[6-{[(2S)-2-(benzyloxycarbonylamino)-3,3-dicyclopropylpropanoyl]amino}-5-(tert-butoxycarbonylamino)pyridin-2-yl]-4-(difluoromethyl)-4-hydroxypiperidine-1-carboxylate To a solution of Intermediate 24 (racemic) (200 mg, 0.44 mmol), Intermediate 25 (146 mg, 0.48 mmol) and pyridine (0.16 mL, 2.00 mmol) in EtOAc (1.25 mL) at 0° C. was added T3P® (50% wt in EtOAc, 0.64 mL, 1.10 mmol) dropwise over 2 minutes. Following the addition, the ice/water bath was removed. The mixture was warmed to r.t. and stirred for 20 h, then quenched by the addition of $H_2O$ (20 mL) and diluted with EtOAc (20 mL). The layers were separated, and the aqueous layer was re-extracted with EtOAc (3×20 mL). The combined organic extracts were washed with saturated aqueous $NaHCO_3$ solution (30 mL), then dried ($Na_2SO_4$) and concentrated in vacuo. Purification by flash chromatography, eluting with EtOAc/isohexane (0-100% gradient), gave the title compound (mixture of two diastereomers) (171 mg, 53%) as a white solid. LCMS (Method 2): $[M+H]^+$ m/z 744.2, RT 1.73 minutes.

Intermediate 28

Benzyl N-[(1S)-2,2-dicyclopropyl-1-{5-[(2S,4R)-4-(difluoromethyl)-4-hydroxypiperidin-2-yl]-1H-imidazo[4,5-b]pyridin-2-yl}ethyl]carbamate trifluoroacetic acid salt Intermediate 27 (mixture of two diastereomers) (171 mg, 0.23 mmol) was dissolved in DCM (1.7 mL) and TFA (0.26 mL, 3.40 mmol) was added. The mixture was heated and stirred at 400 for 20 h, then cooled to r.t., neutralised with saturated aqueous $NaHCO_3$ solution and diluted with EtOAc (10 mL). The layers were separated, and the aqueous layer was re-extracted with EtOAc (2×10 mL). The combined organic extracts were dried ($Na_2SO_4$), then concentrated in vacuo, to give the crude title compound (mixture of two diastereomers) (137 mg, 93%) as a beige foam, which was utilised without further purification. LCMS (Method 2): $[M+H]^+$ m/z 526.2, RT 1.21 minutes.

Intermediate 29

Benzyl N-[(1S)-2,2-dicyclopropyl-1-{5-[(2S,4R)-4-(difluoromethyl)-1-(3-fluorobicyclo-[1.1.1]pentane-1-carbonyl]-4-hydroxypiperidin-2-yl]-1H-imidazo[4,5-b]pyridin-2-yl}-ethyl]carbamate To a solution of Intermediate 28 (mixture of two diastereomers) (137 mg, 0.22 mmol), 3-fluorobicyclo[1.1.1]pentane-1-carboxylic acid (31 mg, 0.24 mmol) and DIPEA (0.15 mL, 0.86 mmol) in DMF (5 mL) at r.t. was added HATU (101 mg, 0.26 mmol) in one portion. The mixture was stirred for 35 minutes, then $H_2O$ (10 mL) was added. The mixture was extracted with EtOAc (2×20 mL) and the combined organic extracts were washed with brine (20 mL), then dried ($Na_2SO_4$) and concentrated in vacuo. Purification by flash chromatography, eluting with EtOAc/isohexane (0-100% gradient), gave the title compound (mixture of two diastereomers) (113 mg, 83%) as a white foam. LCMS (Method 2): $[M+H]^+$ m/z 638.2, RT 1.41 minutes.

Intermediate 30

[(2S,4R)-2-{2-[(1S)-1-Amino-2,2-dicyclopropylethyl]-1H-imidazo[4,5-b]pyridin-5-yl}-4-(difluoromethyl)-4-hydroxypiperidin-1-yl](3-fluorobicyclo[1.1.1]pentan-1-yl)methanone To a solution of Intermediate 29 (mixture of two diastereomers) (113 mg, 0.18 mmol) in EtOH (5 mL) at r.t. was added 10% Pd/C (12 mg). The vessel was evacuated and purged with $H_2$, then left to stir at r.t. for 90 minutes. The mixture was filtered through a pad of Celite® (10 g) under suction, washing through with EtOH (50 mL), and concentrated in vacuo. Purification by flash chromatography (KP-NH column), eluting with EtOAc/isohexane (0-100% gradient), then MeOH/DCM (90:10), gave the title compound (mixture of two diastereomers) (77.6 mg, 87%) as a white solid. LCMS (Method 2): $[M+H]^+$ m/z 504.2, RT 1.17 minutes.

Example 1

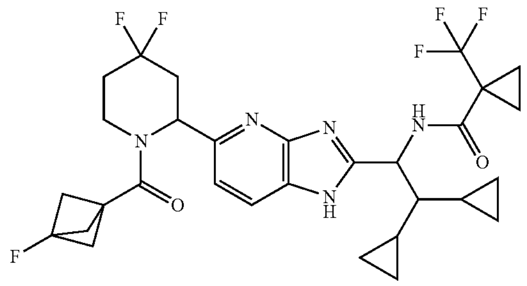 [SMILES: O=C(N1CCC(F)(F)CC1c1ccc2[nH]c(C(NC(=O)C3(C(F)(F)F)CC3)C(C3CC3)C3CC3)nc2n1)C12CC(F)(C1)C2]

N-(2,2-Dicyclopropyl-1-{5-[4,4-difluoro-1-(3-fluorobicyclo[1.1.1]pentane-1-carbonyl)-piperidin-2-yl]-1H-imidazo[4,5-b]pyridin-2-yl}ethyl)-1-(trifluoromethyl)cyclopropane-carboxamide HATU (29.6 mg, 0.0755 mmol) was added to a solution of Intermediate 10 (34.0 mg, 0.0718 mmol) and 1-(trifluoromethyl)cyclopropane-1-carboxylic acid (11.6 mg, 0.0753 mmol) in DMF (0.36 mL). DIPEA (0.038 mL, 0.22 mmol) was added dropwise and the reaction mixture was stirred at r.t. for 2 h, then purified directly (Method 4) and freeze-dried, to give the title compound (14.5 mg, 33%) as a white solid. $\delta_H$ (400 MHz, 373K, DMSO-$d_6$) 12.56 (br s, 1H), 7.91 (d, J 8.3 Hz, 1H), 7.60 (d, J 8.3 Hz, 1H), 7.08 (d, J 8.3 Hz, 1H), 5.77 (d, J 5.7 Hz, 1H), 5.40 (dd, J 8.4, 5.8 Hz, 1H), 4.38 (d, J 14.0 Hz, 1H), 3.44-3.29 (m, 1H), 3.20-3.07 (m, 1H), 2.48-2.31 (m, 7H), 2.12-1.94 (m, 2H), 1.46-1.40 (m, 1H), 1.40-1.34 (m, 1H), 1.31-1.23 (m, 2H), 1.03-0.94 (m, 1H), 0.80-0.69 (m, 2H), 0.48-0.38 (m, 2H), 0.36-0.28 (m, 1H), 0.27-0.16 (m, 3H), 0.12-0.03 (m, 1H), 0.01 to −0.06 (m, 1H). LCMS (Method 5): $[M+H]^+$ m/z 610.4, RT 2.09 minutes.

Example 2

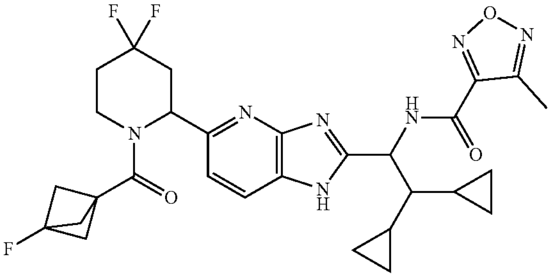 [SMILES: Cc1nonc1C(=O)NC(c1nc2nc(C3CC(F)(F)CCN3C(=O)C34CC(F)(C3)C4)ccc2[nH]1)C(C1CC1)C1CC1]

N-(2,2-Dicyclopropyl-1-{5-[4,4-difluoro-1-(3-fluorobicyclo[1.1.1]pentane-1-carbonyl)-piperidin-2-yl]-1H-imidazo[4,5-b]pyridin-2-yl}ethyl)-4-methyl-1,2,5-oxadiazole-3-carboxamide HATU (562 mg, 1.43 mmol) was added to a solution of Intermediate 10 (0.646 g, 1.37 mmol) and 4-methyl-1,2,5-oxadiazole-3-carboxylic acid (193 mg, 1.43 mmol) in DMF (6.8 mL). DIPEA (0.71 mL, 4.1 mmol) was added dropwise and the reaction mixture was stirred at r.t. for 2 h, then diluted with EtOAc (50 mL) and washed with water (3×50 mL). The combined aqueous layers were extracted with EtOAc (2×35 mL). The organic layers were combined and washed with brine (50 mL), then passed through a phase separator and concentrated in vacuo. The crude residue was purified (Method 6), then freeze-dried, to give the title compound (280 mg, 35%) as a white solid. $\delta_H$ (400 MHz, 373K, DMSO-$d_6$) 12.49 (br s, 1H), 7.87 (d, J 8.2 Hz, 1H), 7.03 (d, J 8.3 Hz, 1H), 5.76 (d, J 6.9 Hz, 1H), 5.55 (d, J 5.7 Hz, 1H), 4.37 (d, J 14.0 Hz, 1H), 3.44-3.32 (m, 1H), 3.21-3.09 (m, 1H), 2.53 (s, 3H), 2.49-2.30 (m, 7H), 2.12-1.94 (m, 2H), 1.11 (td, J 9.0, 5.7 Hz, 1H), 0.95-0.77 (m, 2H), 0.49-0.39 (m, 2H), 0.34-0.20 (m, 4H), 0.13-0.00 (m, 2H). One of the NH proton signals was not visible. LCMS (Method 5): $[M+H]^+$ m/z 584.2, RT 2.00 minutes.

Examples 3 to 6

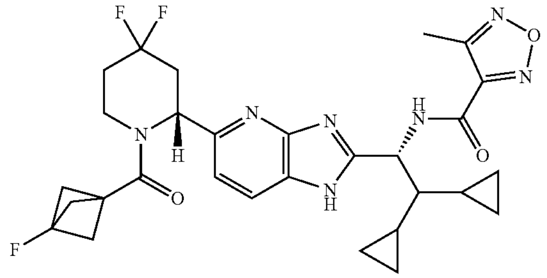

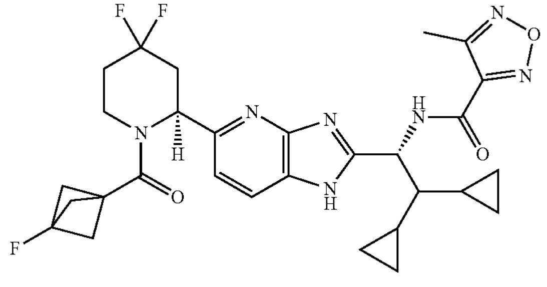

-continued

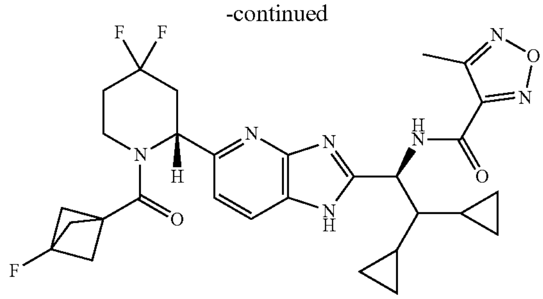

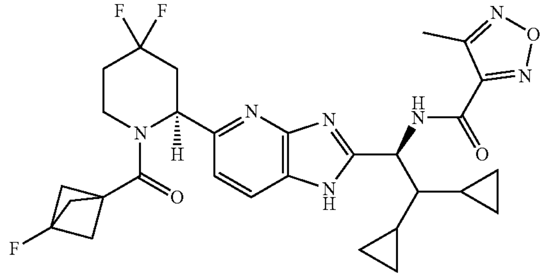

N-[(1R)-2,2-Dicyclopropyl-1-{5-[(2R)-4,4-difluoro-1-(3-fluorobicyclo[1.1.1]pentane-1-carbonyl)piperidin-2-yl]-1H-imidazo[4,5-b]pyridin-2-yl}ethyl)-4-methyl-1,2,5-oxadiazole-3-carboxamide N-[(1R)-2,2-Dicyclopropyl-1-{5-[(2S)-4,4-difluoro-1-(3-fluorobicyclo[1.1.1]pentane-1-carbonyl)piperidin-2-yl]-1H-imidazo[4,5-b]pyridin-2-yl}ethyl)-4-methyl-1,2,5-oxadiazole-3-carboxamide N-[(1S)-2,2-Dicyclopropyl-1-{5-[(2R)-4,4-difluoro-1-(3-fluorobicyclo[1.1.1]pentane-1-carbonyl)piperidin-2-yl]-1H-imidazo[4,5-b]pyridin-2-yl}ethyl)-4-methyl-1,2,5-oxadiazole-3-carboxamide N-[(1S)-2,2-Dicyclopropyl-1-{5-[(2S)-4,4-difluoro-1-(3-fluorobicyclo[1.1.1]pentane-1-carbonyl)piperidin-2-yl]-1H-imidazo[4,5-b]pyridin-2-yl}ethyl)-4-methyl-1,2,5-oxadiazole-3-carboxamide Example 2 (20 mg) was subjected to chiral preparative SFC (Method 7) to give, after lyophilisation, a mixture of unresolved diastereomers (Peaks 1 and 2), and two resolved diastereomers (Peak 3, 0.9 mg; and Peak 4, 0.9 mg) as white solids. The unresolved diastereomers were subjected to further chiral preparative SFC (Method 8) to give, after lyophilisation, two resolved diastereomers (Peak 1, 2.4 mg; and Peak 2, 2.4 mg) as white solids.

Peak 1 (Example 3, arbitrarily assigned as R,R): LCMS (Method 5): $[M+H]^+$ m/z 584.4, RT 2.00 minutes. Chiral analysis (Method 9): RT 2.79 minutes (>90% d.e.).

Peak 2 (Example 4, arbitrarily assigned as R,S): LCMS (Method 5): $[M+H]^+$ m/z 584.4, RT 2.00 minutes. Chiral analysis (Method 9): RT 2.99 minutes (>90% d.e.).

Peak 3 (Example 5, arbitrarily assigned as S,R): LCMS (Method 5): [M+H]+m/z 584.4, RT 2.01 minutes. Chiral analysis (Method 10): RT 3.32 minutes (93.60% d.e.).

Peak 4 (Example 6, arbitrarily assigned as S,S): $\delta_H$ (400 MHz, 373K, DMSO-$d_6$) 12.61 (br s, 1H), 8.75 (br s, 1H), 7.91 (d, J 8.3 Hz, 1H), 7.08 (d, J 8.3 Hz, 1H), 5.77 (d, J 6.9 Hz, 1H), 5.56 (d, J 5.8 Hz, 1H), 4.37 (d, J 13.9 Hz, 1H), 3.43-3.31 (m, 1H), 3.20-3.07 (obs m, 1H), 2.52 (s, 3H), 2.48-2.31 (m, 7H), 2.11-1.94 (m, 2H), 1.12 (td, J 9.0, 5.9 Hz, 1H), 0.92-0.77 (m, 2H), 0.50-0.41 (m, 2H), 0.34-0.21 (m, 4H), 0.12-0.01 (m, 2H). LCMS (Method 5): $[M+H]^+$ m/z 584.2, RT 2.00 minutes. Chiral analysis (Method 10): RT 3.59 minutes (95.38% d.e.).

Examples 7 to 10

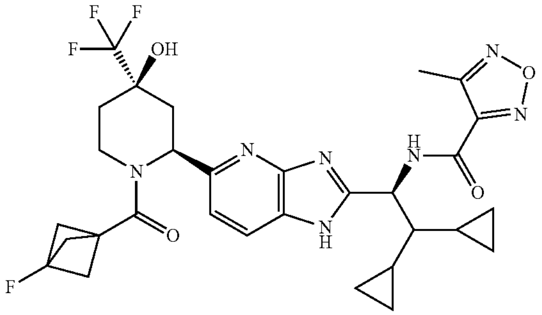

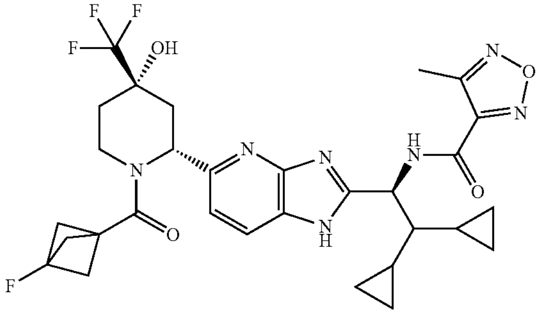

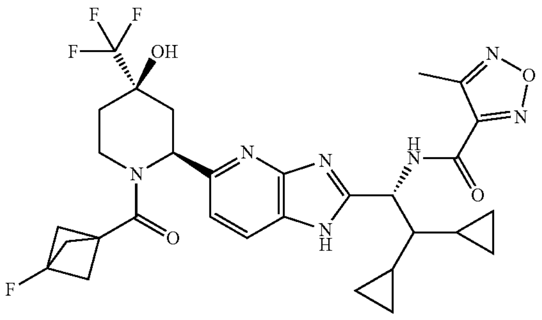

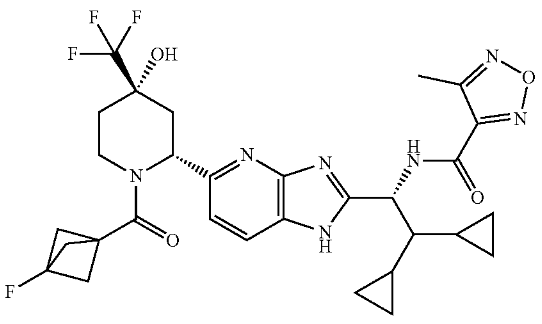

N-[(1S)-2,2-Dicyclopropyl-1-{5-[(2R,4S)-1-(3-fluorobicyclo[1.1.1]pentane-1-carbonyl)-4-hydroxy-4-(trifluoromethyl)piperidin-2-yl]-1H-imidazo[4,5-b]pyridin-2-yl}ethyl]-4-methyl-1,2,5-oxadiazole-3-carboxamide N-[(1S)-2,2-Dicyclopropyl-1-{5-[(2S,4R)-1-(3-fluorobicyclo[1.1.1]pentane-1-carbonyl)-4-hydroxy-4-(trifluoromethyl)piperidin-2-yl]-1H-imidazo[4,5-b]pyridin-2-yl}ethyl]-4-methyl-1,2,5-oxadiazole-3-carboxamide N-[(1R)-2,2-Dicyclopropyl-1-{5-[(2R,4S)-1-(3-fluorobicyclo[1.1.1]pentane-1-carbonyl)-4-hydroxy-4-(trifluoromethyl)piperidin-2-yl]-1H-imidazo[4,5-b]pyridin-2-yl}ethyl]-4-methyl-1,2,5-oxadiazole-3-carboxamide N-[(1R)-2,2-Dicyclopropyl-1-{5-[(2S,4R)-1-(3-fluorobicyclo[1.1.1]pentane-1-carbonyl)-4-hydroxy-4-(trifluoromethyl)piperidin-2-yl]-1H-imidazo[4,5-b]pyridin-2-yl}ethyl]-4-methyl-1,2,5-oxadiazole-3-carboxamide To a solution of Intermediate 20 (mixture of four diastereomers) (237 mg, 0.45 mmol), 4-methyl-1,2,5-oxadiazole-3-carboxylic acid (59 mg, 0.46 mmol) and DIPEA (0.32 mL, 1.80 mmol) in DMF (10 mL) at r.t. was added HATU (214 mg, 0.55 mmol) in one portion. The mixture was stirred for 30 minutes, then water (20 mL) was added and the mixture was extracted with EtOAc (2×20 mL). The combined organic layers were washed with brine (20 mL), then dried ($Na_2SO_4$) and concentrated in vacuo. The residue was purified by flash chromatography, eluting with EtOAc/isohexane (0-100% gradient). The resulting white foam was further purified by chiral SFC (Method 11) to afford, after lyophilisation, the title compounds (Peak 1, 38 mg, 13% yield, 96.8% d.e.; and Peak 2, 30 mg, 10% yield, 98.1% d.e.) as white solids. A third peak was further separated by chiral SFC (Method 12) to afford, after lyophilisation, the title compounds (Peak 3, 23 mg, 8% yield, 100% d.e.; and Peak 4, 29 mg, 10% yield, 100% d.e.) as white solids.

Peak 1: $\delta_H$ (400 MHz, 373K, DMSO-$d_6$) 13.00-12.42 (br s, 1H), 9.03-8.65 (br s, 1H), 7.97 (d, J 8.2 Hz, 1H), 7.21 (d, J 8.3 Hz, 1H), 6.34-5.75 (br s, 1H), 5.58 (t, J 6.7 Hz, 1H), 4.59-3.74 (br s, 1H), 3.50-3.09 (br s, 1H), 2.82-2.56 (br s, 1H), 2.52 (s, 3H), 2.48-2.25 (br s, 7H), 2.16 (dd, J 14.4, 7.3 Hz, 1H), 1.81-1.67 (m, 2H), 1.19-1.08 (m, 1H), 0.94-0.77 (m, 2H), 0.52-0.39 (m, 2H), 0.36-0.20 (m, 4H), 0.15-0.07 (m, 1H), 0.07-0.00 (m, 1H). $^{19}F\{^1H\}$ NMR (282 MHz, 373K, DMSO-$d_6$) δ −82.9 (s, 3F), −147.0 (s, 1F). LCMS (Method 5): $[M+H]^+$ m/z 632, RT 2.44 minutes. Chiral analysis (Method 13): RT 2.65 minutes.

Peak 2: $\delta_H$ (400 MHz, 373K, DMSO-$d_6$) 13.10-12.36 (br s, 1H), 9.03-8.63 (br s, 1H), 7.97 (d, J 8.2 Hz, 1H), 7.21 (d, J 8.3 Hz, 1H), 6.34-5.64 (br s, 1H), 5.57 (s, 1H), 4.50-3.75 (br s, 1H), 3.50-3.11 (br s, 1H), 2.76-2.57 (br s, 1H), 2.52 (s, 3H), 2.48-2.24 (br s, 7H), 2.16 (dd, J 14.4, 7.3 Hz, 1H), 1.82-1.67 (m, 2H), 1.13 (td, J 9.0, 6.0 Hz, 1H), 0.93-0.78 (m, 2H), 0.51-0.42 (m, 2H), 0.36-0.21 (m, 4H), 0.14-0.00 (m, 2H). $^{19}F\{^1H\}$ NMR (282 MHz, 373K, DMSO-$d_6$) δ −82.8 (s, 3F), −147.0 (s, 1F). LCMS (Method 5): $[M+H]^+$ m/z 632, RT 2.44 minutes. Chiral analysis (Method 13): RT 2.87 minutes.

Peak 3: $\delta_H$ (400 MHz, 373K, DMSO-$d_6$) 12.90 (s, 1H, benzimidazole NH tautomer), 12.56 (s, 1H, benzimidazole NH tautomer), 8.91 (d, J 8.5 Hz, 1H, tautomer), 8.76 (d, J 8.2

Hz, 1H, tautomer), 7.98 (app t, J 8.2 Hz, 1H), 7.27 (d, J 7.4 Hz, 1H, tautomer), 7.19 (d, J 8.3 Hz, 1H, tautomer), 6.35-5.65 (br s, 1H), 5.57 (s, 1H), 4.51-3.74 (br s, 1H), 3.48-3.08 (br s, 1H), 2.77-2.55 (br s, 1H), 2.52 (s, 3H), 2.47-2.28 (br s, 7H), 2.16 (dd, J 14.4, 7.3 Hz, 1H), 1.81-1.68 (m, 2H), 1.20-1.07 (m, 1H), 0.93-0.77 (m, 2H), 0.51-0.41 (m, 2H), 0.36-0.21 (m, 4H), 0.16-0.00 (m, 2H). $^{19}F$ $\{^1H\}$ NMR (282 MHz, 373K, DMSO-$d_6$) δ −82.9 (s, 3F), −147.0 (s, 1F). LCMS (Method 5): $[M+H]^+$ m/z 632, RT 2.46 minutes. Chiral analysis (Method 14): RT 2.39 minutes.

Peak 4: $\delta_H$ (400 MHz, 373K, DMSO-$d_6$) 12.97-12.49 (br s, 1H), 8.98-8.66 (br s, 1H), 7.96 (d, J 8.2 Hz, 1H), 7.21 (d, J 8.3 Hz, 1H), 6.34-5.67 (br s, 1H), 5.57 (s, 1H), 4.51-3.62 (br s, 1H), 3.43-3.11 (br s, 1H), 2.78-2.55 (br s, 1H), 2.52 (s, 3H), 2.47-2.27 (br s, 7H), 2.16 (dd, J 14.4, 7.3 Hz, 1H), 1.80-1.67 (m, 2H), 1.13 (td, J 9.0, 6.0 Hz, 1H), 0.93-0.77 (m, 2H), 0.51-0.39 (m, 2H), 0.36-0.20 (m, 4H), 0.15-0.07 (m, 1H), 0.07-0.00 (m, 1H). $^{19}F$ $\{^1H\}$ NMR (282 MHz, 373K, DMSO-$d_6$) δ −82.9 (s, 3F), −147.0 (s, 1F). LCMS (Method 5): $[M+H]^+$ m/z 632, RT 2.46 minutes. Chiral analysis (Method 14): RT 2.98 minutes.

Examples 11 & 12

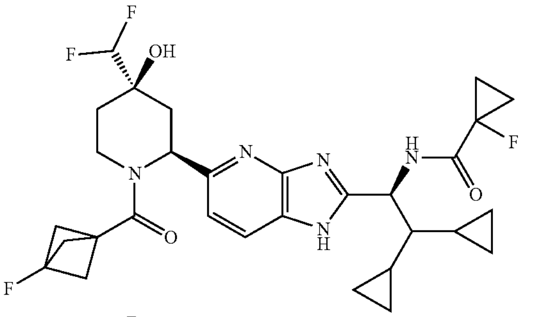

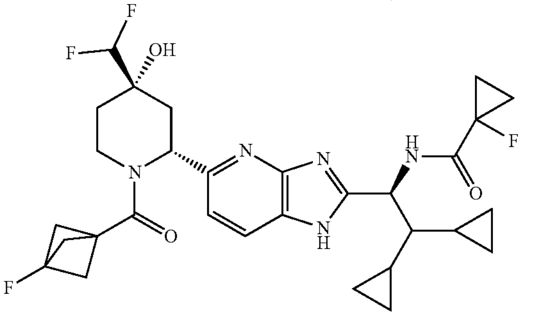

N-[(1S)-2,2-Dicyclopropyl-1-{5-[(2S,4R)-4-(difluoromethyl)-1-(3-fluorobicyclo[1.1.1]-pentane-1-carbonyl)-4-hydroxypiperidin-2-yl]-1H-imidazo[4,5-b]pyridin-2-yl}ethyl]-1-fluorocyclopropanecarboxamide N-[(1S)-2,2-Dicyclopropyl-1-{5-[(2R,4S)-4-(difluoromethyl)-1-(3-fluorobicyclo[1.1.1]-pentane-1-carbonyl)-4-hydroxypiperidin-2-yl]-1H-imidazo[4,5-b]pyridin-2-yl}ethyl]-1-fluorocyclopropanecarboxamide To a solution of Intermediate 30 (mixture of two diastereomers) (38.8 mg, 0.0770 mmol), 1-fluorocyclopropane carboxylic acid (9.0 mg, 0.0856 mmol) and DIPEA (0.06 mL, 0.30 mmol) in DMF (4 mL) at r.t. was added HATU (36.0 mg, 0.092 mmol) in one portion. The mixture was stirred for 30 minutes, then $H_2O$ (10 mL) was added. The mixture was extracted with EtOAc (2×20 mL) and the combined organic extracts were washed with brine (20 mL), then dried ($Na_2SO_4$) and concentrated in vacuo. The residue was purified by flash chromatography, eluting with EtOAc/isohexane (0-100% gradient). Chiral purification of the resulting white foam (40.0 mg) was performed by SFC (using a (R,R) Whelk-O1 250×20 mm, 5 μm column; flow rate: 100 mL/minute; column temperature: 40° C.; eluting with a 3-40% MeOH (+0.1% $NH_4OH$) method (ABPR 60 bar), using a 7.5 minute run time on a Waters Prep 100 fractionlynx system, in tandem with a Waters SQD2 mass spectrometer) to afford, after lyophilisation, the title compounds (Peak 1, RT 5.06 minutes, 10.0 mg, 22.0%, >99% d.e.; and Peak 2, RT 5.44 minutes, 11.0 mg, 24.2%, 97.9% d.e.).

Peak 1: $\delta_H$ (400 MHz, 373K, DMSO-$d_6$) 13.00-12.30 (br s, 1H), 7.97 (d, J 9.0 Hz, 1H), 7.91 (d, J 8.2 Hz, 1H), 7.16 (d, J 8.2 Hz, 1H), 6.25-5.79 (br s, 1H), 5.74 (t, J 56.6 Hz, 1H), 5.42 (dd, J 8.5, 6.0 Hz, 1H), 4.33-3.71 (br s, 1H), 3.46-3.08 (br s, 1H), 2.45-2.31 (m, 7H), 2.03 (dd, J 14.4, 7.4 Hz, 1H), 1.70-1.56 (m, 2H), 1.40-1.17 (m, 4H), 1.08-0.98 (m, 1H), 0.88-0.71 (m, 2H), 0.49-0.30 (m, 3H), 0.30-0.17 (m, 3H), 0.15-0.06 (m, 1H), 0.06 to −0.02 (m, 1H). The OH proton signal was not observed. LCMS (Method 5): [M+H]+ m/z 590.4, RT 1.86 minutes. Chiral analysis (Method 16): RT 5.10 minutes.

Peak 2: $\delta_H$ (400 MHz, 373K, DMSO-$d_6$) 13.00-12.45 (br s, 1H), 7.96 (d, J 8.8 Hz, 1H), 7.93 (d, J 8.3 Hz, 1H), 7.18 (d, J 8.2 Hz, 1H), 6.27-5.68 (br s, 1H), 5.74 (t, J 56.6 Hz, 1H), 5.44 (dd, J 8.8, 6.1 Hz, 1H), 4.33-3.71 (br s, 1H), 3.48-3.11 (br s, 1H), 2.45-2.35 (m, 7H), 2.04 (dd, J 14.5, 7.2 Hz, 1H), 1.68-1.55 (m, 2H), 1.40-1.18 (m, 4H), 1.08-0.98 (m, 1H), 0.85-0.70 (m, 2H), 0.50-0.31 (m, 3H), 0.30-0.18 (m, 3H), 0.16-0.07 (m, 1H), 0.05 to −0.04 (m, 1H). The OH proton signal was not observed. LCMS (Method 5): $[M+H]^+$ m/z 590.4, RT 1.86 minutes. Chiral analysis (Method 16): RT 5.49 minutes.

The invention claimed is:

1. A compound of formula (I) or an N-oxide thereof, or a pharmaceutically acceptable salt thereof:

(I)

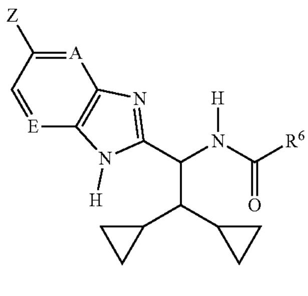

wherein

A represents N;

E represents C—$R^2$;

Z represents a group of formula (Zc):

(Zc)

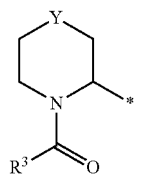

in which the asterisk (*) represents the point of attachment to the remainder of the molecule;

Y represents —$CR^{5a}R^{5b}$;

$R^2$ represents hydrogen;

$R^3$ represents $C_{4-12}$ bicycloalkyl, which group may be optionally substituted by one, two, three or four substituents independently selected from halogen;

$R^{5a}$ represents fluoro, difluoromethyl or trifluoromethyl;

$R^{5b}$ represents fluoro, or hydroxy; and $R^6$ represents $C_{3-9}$ cycloalkyl (including benzo-fused analogues thereof) or heteroaryl, either of which groups may be optionally substituted by one, two or three substituents independently selected from halogen, $C_{1-6}$ alkyl and trifluoromethyl.

2. A compound as claimed in claim 1 represented by formula (IIA) or an N-oxide thereof, or a pharmaceutically acceptable salt thereof:

(IIA)

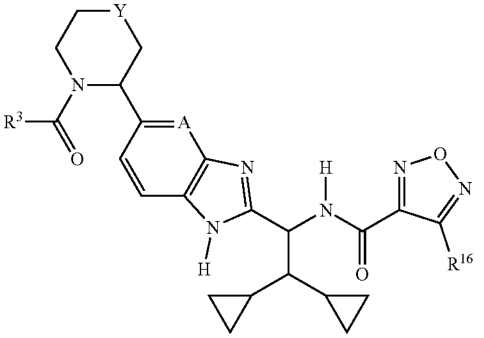

wherein $R^{16}$ represents methyl or ethyl.

3. A compound as claimed in claim 1 represented by formula (IIB) or an N-oxide thereof, or a pharmaceutically acceptable salt thereof:

(IIB)

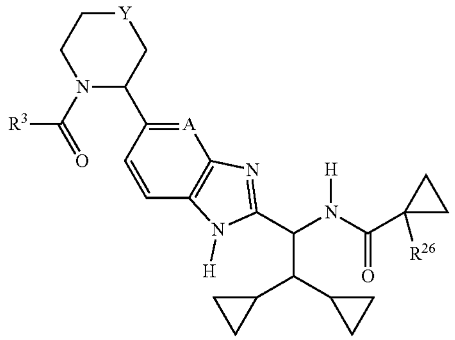

wherein $R^{26}$ represents fluoro or trifluoromethyl.

4. A compound as claimed in claim 1 which is

N-(2,2-Dicyclopropyl-1-{5-[4,4-difluoro-1-(3-fluorobicyclo[1.1.1]pentane-1-carbonyl)-piperidin-2-yl]-1H-imidazo[4,5-b]pyridin-2-yl}ethyl)-1-(trifluoromethyl) cyclopropane-carboxamide;

N-(2,2-Dicyclopropyl-1-{5-[4,4-difluoro-1-(3-fluorobicyclo[1.1.1]pentane-1-carbonyl)-piperidin-2-yl]-1H-imidazo[4,5-b]pyridin-2-yl}ethyl)-4-methyl-1,2,5-oxadiazole-3-carboxamide;

N-[(1R)-2,2-Dicyclopropyl-1-{5-[(2R)-4,4-difluoro-1-(3-fluorobicyclo[1.1.1]pentane-1-carbonyl)piperidin-2-yl]-1H-imidazo[4,5-b]pyridin-2-yl}ethyl)-4-methyl-1,2,5-oxadiazole-3-carboxamide;

N-[(1R)-2,2-Dicyclopropyl-1-{5-[(2S)-4,4-difluoro-1-(3-fluorobicyclo[1.1.1]pentane-1-carbonyl)piperidin-2-yl]-1H-imidazo[4,5-b]pyridin-2-yl}ethyl)-4-methyl-1,2,5-oxadiazole-3-carboxamide;

N-[(1S)-2,2-Dicyclopropyl-1-{5-[(2R)-4,4-difluoro-1-(3-fluorobicyclo[1.1.1]pentane-1-carbonyl)piperidin-2-yl]-1H-imidazo[4,5-b]pyridin-2-yl}ethyl)-4-methyl-1,2,5-oxadiazole-3-carboxamide;

N-[(1S)-2,2-Dicyclopropyl-1-{5-[(2S)-4,4-difluoro-1-(3-fluorobicyclo[1.1.1]pentane-1-carbonyl)piperidin-2-yl]-1H-imidazo[4,5-b]pyridin-2-yl}ethyl)-4-methyl-1,2,5-oxadiazole-3-carboxamide;

N-[(1S)-2,2-Dicyclopropyl-1-{5-[(2R,4S)-1-(3-fluorobicyclo[1.1.1]pentane-1-carbonyl)-4-hydroxy-4-(trifluoromethyl)piperidin-2-yl]-1H-imidazo[4,5-b]pyridin-2-yl}ethyl]-4-methyl-1,2,5-oxadiazole-3-carboxamide;

N-[(1S)-2,2-Dicyclopropyl-1-{5-[(2S,4R)-1-(3-fluorobicyclo[1.1.1]pentane-1-carbonyl)-4-hydroxy-4-(trifluoromethyl)piperidin-2-yl]-1H-imidazo[4,5-b]pyridin-2-yl}ethyl]-4-methyl-1,2,5-oxadiazole-3-carboxamide;

N-[(1R)-2,2-Dicyclopropyl-1-{5-[(2R,4S)-1-(3-fluorobicyclo[1.1.1]pentane-1-carbonyl)-4-hydroxy-4-(trifluoromethyl)piperidin-2-yl]-1H-imidazo[4,5-b]pyridin-2-yl}ethyl]-4-methyl-1,2,5-oxadiazole-3-carboxamide;

N-[(1R)-2,2-Dicyclopropyl-1-{5-[(2S,4R)-1-(3-fluorobicyclo[1.1.1]pentane-1-carbonyl)-4-hydroxy-4-(trifluoromethyl)piperidin-2-yl]-1H-imidazo[4,5-b]pyridin-2-yl}ethyl]-4-methyl-1,2,5-oxadiazole-3-carboxamide;

N-[(1S)-2,2-Dicyclopropyl-1-{5-[(2S,4R)-4-(difluoromethyl)-1-(3-fluorobicyclo[1.1.1]-pentane-1-carbonyl)-4-hydroxypiperidin-2-yl]-1H-imidazo[4,5-b]pyridin-2-yl}ethyl]-1-fluorocyclopropanecarboxamide;

N-[(1S)-2,2-Dicyclopropyl-1-{5-[(2R,4S)-4-(difluoromethyl)-1-(3-fluorobicyclo[1.1.1]-pentane-1-carbonyl)-4-hydroxypiperidin-2-yl]-1H-imidazo[4,5-b]pyridin-2-yl}ethyl]-1-fluorocyclopropanecarboxamide;

or a pharmaceutically acceptable salt thereof.

5. A pharmaceutical composition comprising a compound of formula (I) as defined in claim 1 or an N-oxide thereof, or a pharmaceutically acceptable salt thereof, in association with a pharmaceutically acceptable carrier.

6. A pharmaceutical composition as claimed in claim 5 further comprising an additional pharmaceutically active ingredient.

7. A method for the treatment of an inflammatory or autoimmune disorder selected from psoriasis, psoriatic arthritis, hidradenitis suppurativa, axial spondylo-arthritis and ankylosing spondylitis, which comprises administering to a patient in need of such treatment an effective amount of a compound of formula (I) as defined in claim 1 or an N-oxide thereof, or a pharmaceutically acceptable salt thereof.

* * * * *